United States Patent
Gozlan et al.

(10) Patent No.: US 10,874,103 B2
(45) Date of Patent: Dec. 29, 2020

(54) ANTIBACTERIAL COMPOSITION COMPRISING AN ACETAL OR A LONG-CHAIN ALKYL HEXITANE ETHER

(71) Applicants: TEREOS STARCH & SWEETENERS BELGIUM, Aalst (BE); UNIVERSITÉ CLAUDE BERNARD LYON 1, Villeurbanne (FR); CENTRE NATIONAL DE LA RECHERCHE SCIENTIFIQUE (C.N.R.S.), Paris (FR)

(72) Inventors: Charlotte Gozlan, Villeurbanne (FR); Dorine Belmessieri, Villeurbanne (FR); Marie-Christine Duclos, Villeurbanne (FR); Nicolas Duguet, Villeurbanne (FR); Marc Lemaire, Villeurbanne (FR); Gérard Lina, Villeurbanne (FR); Oana Dumitrescu, Villeurbanne (FR); Andreas Redl, Aalst (BE)

(73) Assignee: TEREOS STARCH & SWEETENERS BELGIUM (BE)

(*) Notice: Subject to any disclaimer, the term of this patent is extended or adjusted under 35 U.S.C. 154(b) by 141 days.

(21) Appl. No.: 15/537,871

(22) PCT Filed: Dec. 17, 2015

(86) PCT No.: PCT/IB2015/059733
§ 371 (c)(1),
(2) Date: Jun. 19, 2017

(87) PCT Pub. No.: WO2016/098048
PCT Pub. Date: Jun. 23, 2016

(65) Prior Publication Data
US 2018/0000077 A1    Jan. 4, 2018

(30) Foreign Application Priority Data

Dec. 17, 2014 (FR) ................................. 14 02894

(51) Int. Cl.
| | |
|---|---|
| A61K 31/341 | (2006.01) |
| A61K 31/7004 | (2006.01) |
| A01N 43/08 | (2006.01) |
| A61Q 17/00 | (2006.01) |
| A61K 31/7028 | (2006.01) |
| A23L 5/00 | (2016.01) |
| A61K 8/33 | (2006.01) |
| A23L 3/3463 | (2006.01) |
| C11D 3/43 | (2006.01) |
| C07D 407/04 | (2006.01) |
| C07D 307/20 | (2006.01) |
| C07D 493/04 | (2006.01) |
| A23L 3/3544 | (2006.01) |
| A61K 8/34 | (2006.01) |
| A61K 8/49 | (2006.01) |

(52) U.S. Cl.
CPC ............ *A01N 43/08* (2013.01); *A23L 3/3463* (2013.01); *A23L 3/3544* (2013.01); *A23L 5/00* (2016.08); *A61K 8/33* (2013.01); *A61K 8/345* (2013.01); *A61K 8/4973* (2013.01); *A61K 31/341* (2013.01); *A61K 31/7004* (2013.01); *A61K 31/7028* (2013.01); *A61Q 17/005* (2013.01); *C07D 307/20* (2013.01); *C07D 407/04* (2013.01); *C07D 493/04* (2013.01); *C11D 3/43* (2013.01); *A61K 2800/522* (2013.01)

(58) Field of Classification Search
CPC ...................................................... A61Q 7/005
See application file for complete search history.

(56) References Cited

U.S. PATENT DOCUMENTS

2014/0316148 A1* 10/2014 Tulchinsky .......... C07D 307/12
549/473

FOREIGN PATENT DOCUMENTS

| EP | 092998 A1 | 11/1983 |
|---|---|---|
| JP | H1115114 A | 1/1999 |
| WO | WO2012/148530 A1 | 11/2012 |
| WO | WO2014/025413 A1 | 2/2014 |
| WO | WO2014/199345 A1 | 12/2014 |
| WO | WO2015/189796 A1 | 12/2015 |

OTHER PUBLICATIONS

Sarney et al.,, Biotechnology and Bioengineering, 54(4), 1997, 351-356.*
Written Opinion and International Search Report dated Feb. 16, 2016.
Shuichi Matsumura et al: Surface activities, biodegradability and antimicrobial properties of n-alkyl glucosides, mannosides and galactosides11, Journal of the American Oil Chemists' Society, vol. 67, No. 12, Dec. 1, 1990 (Dec. 1, 1990), pp. 996-1001, XP055029089,ISSN: 0003-021X, DOI: 10.1007/BF02541865 tablespage 1000.
Peter Koll et al: "Carbohydrate-Based Liquid Crystals: Mesogenic 1-0-Alkyl Derivatives of 2,5-Anhydrohexitols", ANG EWAN DTE Chemie. International Edition., vol. 25, No. 4, Apr. 1, 1986 (Apr. 1, 1986), pp. 368-369, XP055249595, DE.

* cited by examiner

*Primary Examiner* — Kyle A Purdy
(74) *Attorney, Agent, or Firm* — FRESH IP PLC; Clifford D. Hyra; Aubrey Y. Chen

(57) ABSTRACT

A bactericidal or bacteriostatic composition comprising an acetal or a hexitan ether preferentially of a long-chain alkyl sorbitan, arlitan or mannitan, its use in the treatment or prevention of Gram-positive bacterial infections, its use as a hygiene or dermatological product for external use and a method for disinfecting surfaces.

16 Claims, No Drawings

ANTIBACTERIAL COMPOSITION COMPRISING AN ACETAL OR A LONG-CHAIN ALKYL HEXITANE ETHER

This application claims the benefit of French patent application 14/02894, filed Dec. 17, 2014, which is hereby incorporated by reference in its entirety.

TECHNICAL DOMAIN

Embodiments of the present invention relates to a bactericidal or bacteriostatic composition comprising an acetal or a long-chain alkyl hexitan ether, its use in the treatment or prevention of Gram-positive bacterial infections, its use as a hygiene or dermatological product for external use and a method for disinfecting surfaces.

TECHNICAL BACKGROUND

Antimicrobial compounds are defined as molecules that can inhibit or stop the growth of micro-organisms or kill them. In this context, they are commonly used to prevent or treat human and animal infections, and in the agrifood industry to prevent multiplication of pathogenic bacteria in food. Widespread use of antimicrobial compounds favors the emergence of resistant infectious agents. The spread of bacteria that has acquired resistance mechanisms for the most widely used antimicrobial compounds is a more and more alarming major public health problem (J. S. Bradley et al. Lancet Infect. Dis. 2007; 7:68-78).

As an illustration, many strains resistant to antibiotics for the most pathogenic species of genus *Staphylococcus*, i.e. *Staphylococcus aureus*, have been isolated. *Staphylococcus* infections represent a high percentage of serious infections. What is more, almost half of nosocomial infections are reportedly related to *staphylococcus*. Mention may be made of the many strains of *Enterococcus faecalis* or *Enterococcus faecium* that are resistant to commonly used antibiotics. Although they are less virulent than *Staphylococci* in particular, an increasing number of multiresistant *Enterococcus* strains and more recently epidemics of enterococci resistant to glycopeptides, the antibiotics of recourse for this bacterial family, have been identified.

Another antibioresistance phenomenon has been described that might not only be related to the excessive use of antibiotics, but to food storage methods. So for example it has been shown that *Listeria monocytogenes* is more resistant to antibiotics after having undergone osmotic stress, at a low temperature or in an acidic medium (Anas A. et al. (2015) Food Microbiology, Volume 46, April, Pages 154-160). That is, the human contamination comes from food. In addition, although it is relatively rare, human listeriosis is a serious infection with mortality estimated at 50%. Accordingly, the emergence of antibiotic resistance in *L. monocytogenes* that could be caused by modern storage or treatment methods for food constitutes a serious threat to public health.

Although several mechanisms are often involved simultaneously in antibiotic resistance, it is common to classify it into three categories: (a) lack of antibiotic penetration into the bacterium, (b) inactivation or excretion of the antibiotic by bacterial enzymatic systems and (c) lack of affinity between the bacterial target and the antibiotic. These three resistance mechanism categories have a structural component, i.e. the mechanisms used are dependent on the structure of the molecule concerned.

No process in the prior art can produce an isomeric mixture of biosourced compounds with low toxicity and low cost.

Nevertheless, biosourced compounds have been described. Accordingly, different compounds used as antimicrobials have been described, among which are fatty acids and their corresponding polyhydroxylated esters that are active against Gram-positive bacteria and having long aliphatic chains. As an indication, one of the most active antimicrobials is monolaurin, a glycerol monoester with a C12 aliphatic chain. Its trade name is LAURICIDIN®. This compound is used as a food additive to inhibit bacterial growth (E. Freese, C. W. Sheu, E. Gathers. *Nature* 1973, 241, 321-325; E. G. A. Verhaegh, D. L. Marshall, D.-H. Oh. *Int. J. Food Microbiol.* 1996, 29, 403-410). The ester function of the monolaurin is sensitive to esterases, so this compound degrades quickly and has a short half-life.

Also described are antimicrobials derived from sugar considered as particularly attractive because of their biodegradability, their low toxicity and environmental impact.

Examples of antimicrobials derived from sugar are the esters derived from sugar that are also used industrially for antimicrobial applications because their raw materials and production costs remain relatively low. Mention may be made for example of sorbitan caprylate described in international patent application WO2014/025413 in mixture with Hinokitiol in an antimicrobial formulation. According to this application, this formulation will inhibit or kill Gram-positive and -negative bacteria, fungi and/or yeast.

Also described is the use of disaccharide esters as antimicrobial agents in the food industry. Dodecanoyl sucrose is one of the most used. It is reportedly particularly active against *L. monocytogenes* (M Ferrer, I Soliveri, F. J. Plou, N. López-Cortes, D. Reyes-Duarte, M Christensen, J. L. Copa-Patiño, A. Ballesteros, *Enz. Microb. Tech.*, 2005, 36, 391-398). Nevertheless, it is also described as weakly inhibiting the growth of *S. aureus*, for hospital applications (J. D. Monk, L. R. Beuchat, A. K. Hathcox, *J. Appl. Microbiol.*, 1996, 81, 7-18). It reports that the sucrose ester presents properties that are bacteriostatic (stops bacterial growth) but not bactericidal (kills the bacteria).

In addition, the synthesis of sugar esters presents many drawbacks. First, in spite of the low production cost, synthesizing esters, more particularly for di- and trisaccharides, is problematic because of sugars' high functionality, which causes the formation of a mixture of mono-, di- and polyesters and the presence of a polar solvent, such as dimethylformamide (DMF) and pyridine, is generally necessary to better solubilize the highly polar reagents. However, these solvents are classed carcinogenic, mutagenic and reprotoxic (CMR) and their use must be avoided. To solve this problem, enzymatic synthesis was used but the need to use very dilute media in these conditions makes production limited.

Moreover, the ester functions on these compounds are easy for the esterases present in the cells to hydrolyze. The molecules released after this hydrolysis, i.e. the sugar and the fatty acid, have little or no antimicrobial properties (the fatty acid is slightly active). This causes instability that is responsible for reduced activity in these compounds.

SUMMARY

To produce an antibiotic composition having lower chances of allowing resistance to develop, a composition may be used containing a mixture of compounds having antibiotic activity but including structural differences that can reduce the chances of developing bacterial resistance, in particular, a composition comprising an isomeric mixture of compounds having antibiotic activity.

A new antibiotic composition has low toxicity and low environmental impact. A biodegradable composition that can be obtained in large quantities from renewable resources, at low cost to be perfectly accessible for industrial application but also as effective as non-biosourced antimicrobials.

To produce an antibiotic composition that is not prone to develop resistance comprising effective and stable antimicrobial agents, embodiments of the invention propose an alkyl acetal or a long-chain alkyl sorbitan alkyl ether having very good antimicrobial activity whether in its pure form or as a mixture of isomers, where such a product can be obtained in particular in conditions that are not costly while respecting the environment and not representing a hazard for topical applications or by ingestion.

DETAILED DESCRIPTION OF EMBODIMENTS

Bactericidal or Bacteriostatic Composition

Embodiments of the invention relate to a bactericidal or bacteriostatic composition comprising an alkyl acetal or a hexitan alkyl ether preferentially of sorbitan, arlitan or mannitan in which the alkyl group comprises between 11 to 18 carbon atoms, a pharmaceutically acceptable salt, an isomer or a mixture of isomers thereof. Preferentially, said alkyl acetal or alkyl ether group is in the 2-O, 3-O, 5-O and/or 6-O position. Advantageously, said alkyl acetal group is in the 2,3-O; 3,5-O or 5,6-O position. Advantageously, said alkyl ether group is in the 2-O, 3-O, 5-O or 6-0 position.

The term "pharmaceutically acceptable salt" denotes any salt that, through administration to the patient, can provide (directly or indirectly) a compound such as that described herein. The preparation of salts may be achieved through processes known in the state of the art.

According to the invention, a "hexitan" is obtained by dehydrating a hydrogenated hexose (or hexitol) such as a sorbitol or mannitol. Typically, the hexitan is chosen from sorbitan, arlitan or mannitan. Advantageously, the hexitan is chosen from 1,4-anhydro-D-sorbitol (1,4-arlitan or sorbitan); 1,5-anhydro-D-sorbitol (polygalitol); 3,6-anhydro-D-sorbitol (3,6-sorbitan); 1,4 (3,6)-anhydro-D-mannitol (mannitan); 1,5-anhydro-D-mannitol (styracitol); 3,6-anhydro-D-galactitol; 1,5-anhydro-D-galactitol; 1,5-anhydro-D-talitol and 2,5-anhydro-L-iditol.

Such a sorbitan acetal may be obtained by methods known to the person skilled in the art such as direct acetalization, trans-acetalization for example. In addition, a sorbitan alkyl ether may be obtained by methods known to the person skilled in the art such as the Williamson ether synthesis, epoxide opening, alcohol condensation, alcohol telomerization, acetal reduction, direct or indirect reducing alkylation.

A method produces this derivative in the pure form or in the form of a mixture of isomers of monoethers or hexitan alkyl monoacetals; preferentially the isomers are positional isomers and/or diastereoisomers.

A bactericidal or bacteriostatic composition comprises a hexitan alkyl monoether or monoacetal or a mixture of isomers thereof, preferentially positional isomers, obtained by a process comprising the following steps:

a) a dehydration of a hexitol to obtain a monoanhydrohexitol;

b) an acetalization or trans-acetalization of the hexitol or monoanhydrohexitol obtained in a) by an aliphatic aldehyde containing from 11 to 18 carbon atoms or the acetal thereof, typically by
  i. an aliphatic aldehyde containing from 11 to 18 carbon atoms, by acetalization, or
  ii. an aliphatic aldehyde derivative containing from 11 to 18 carbon atoms, by trans-acetalization;

c) optionally, catalytic hydrogenolysis of the hexitan alkyl acetal obtained in b) preferentially without an acid catalyst, d) recovery of a mixture of hexitan alkyl monoether isomers obtained in c) in which the alkyl group (R) comprises between 11 to 18 carbon atoms
  or
  recovery of a mixture of hexitan alkyl monoacetal isomers obtained in b) in which the alkyl group (R) comprises between 11 to 18 carbon atoms, and e) optionally, purification of either of the mixtures obtained in d), in particular by chromatography.

A bactericidal or bacteriostatic composition comprises a sorbitan alkyl monoether or monoacetal or a mixture of isomers thereof, preferentially positional isomers, obtained by a process comprising the following steps:

a) a dehydration of a sorbitol to obtain a monoanhydrosorbitol;

b) an acetalization or trans-acetalization of the sorbitol or monoanhydrosorbitol obtained in a) by an aliphatic aldehyde containing from 11 to 18 carbon atoms or the acetal thereof, typically by
  i. an aliphatic aldehyde containing from 11 to 18 carbon atoms, by acetalization, or
  ii. an aliphatic aldehyde derivative containing from 11 to 18 carbon atoms, by trans-acetalization;

c) optionally, catalytic hydrogenolysis of the sorbitan alkyl acetal obtained in b) preferentially without an acid catalyst, d) recovery of a mixture of sorbitan alkyl monoether isomers obtained in c) in which the alkyl group (R) comprises between 11 to 18 carbon atoms
  or
  recovery of a mixture of sorbitan alkyl monoacetal isomers obtained in b) in which the alkyl group (R) comprises between 11 to 18 carbon atoms, and e) optionally, purification of either of the mixtures obtained in d), in particular by chromatography.

Typically, the aliphatic aldehyde derivative may be a di-alkyl acetal of the corresponding aldehyde. Di-methyl acetals and di-ethyl acetals are preferred.

A "monoanhydrohexitol" or a "monoanhydrosorbitol" is obtained by dehydration, by the elimination of one or more molecules of water from a hexitol or sorbitol. A suitable example monoanhydrosorbitol may be 1,4-anhydro-D-sorbitol (1,4-arlitan or sorbitan); 1,5-anhydro-D-sorbitol (polygalitol) or 3,6-anhydro-D-sorbitol (3,6-sorbitan).

The preferred monoanhydrosorbitol is a derivative from the dehydration of sorbitol to form, for example, 1,4-sorbitan, 3,6-sorbitan or 2,5-sorbitan.

"Positional isomer" is understood to mean regioisomers, more particularly understood to mean isomers of hexitan alkyl monoethers or monoacetals and in particular of sorbitan in which the alkyl monoether or monoacetal group is positioned on a different hexitan carbon. Typically, the positional isomers of the sorbitan alkyl monoacetal are 2,3-O-; 3,5-O- or 5,6-O- sorbitan alkyl monoacetal. Isomers of sorbitan alkyl monoether are 2-O-, 3-O-, 5-O- or 6-O-sorbitan alkyl monoether.

The term "diastereoisomers" denotes optical isomers that are not superimposable, nor mirror images. Examples of sorbitan alkyl monoacetal diastereoisomers are:

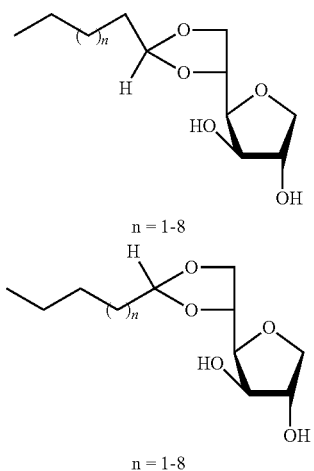

n = 1-8 n = 1-8

According to an embodiment, the process according to the invention may comprise a hexitol dehydration step to obtain a monoanhydrohexitol. Typically, the sorbitol is melted before the dehydration step. The dehydration step may be conducted with a catalyst, for example with an acidic catalyst.

The dehydration step may be conducted under a hydrogen atmosphere at a pressure preferably of about 20 to 50 bar.

Advantageously, the dehydration step is conducted at a temperature comprised between 120 and 170° C., preferably between 130 and 140° C.

Typically, the sorbitol is purified after the dehydration step, for example by crystallization, recrystallization or chromatography.

The acetalization or trans-acetalization step may comprise:

i) optionally, a step of preheating sorbitol, preferably at a temperature comprised between 70 and 130° C., typically between 90 and 110° C., ii) a step of addition of the aliphatic aldehyde or an aliphatic aldehyde derivative of said sorbitol and iii) a step of addition of a catalyst, preferably an acid catalyst.

Step i) is particularly advantageous in that it may be implemented in the absence of solvent.

Preferably, the acid catalyst used during the acetalization or trans-acetalization step and if need be the dehydration step may be a homogeneous or heterogeneous acid catalyst. The term "homogeneous", as used in the expression "homogeneous acid catalyst", refers to a catalyst that is in the same phase (solid, liquid or gas) or in the same aggregate state as the reagent. Conversely, the term "heterogeneous," as used in the expression "heterogeneous acid catalyst", refers to a catalyst that is in a different phase (solid, liquid or gas) as the reagents.

Said acid catalyst used during the acetalization or trans-acetalization step and if need be during the dehydration step may be independently chosen from solid or liquid, organic or inorganic acids, solid acids being preferred. Specifically, the preferred acid catalyst is chosen from para-toluene sulfonic acid, methane sulfonic acid, camphorsulfonic acid (CSA) and sulfonic resins.

Typically, the acetalization or trans-acetalization step is conducted at temperatures comprised between 70 and 130° C., typically between 70 and 90° C. The temperature of the reaction mixtures may vary as a function of the reagents and solvents used. The reaction time is determined by the degree of conversion reached.

According to an embodiment, the acetalization or trans-acetalization step may be conducted by an aliphatic aldehyde or the acetal thereof, typically a linear or branched aliphatic aldehyde or the acetal thereof. The acetalization or trans-acetalization step may be typically conducted with an aliphatic aldehyde or the acetal thereof having 11, 12, 13, 14, 15, 16, 17 or 18 carbon atoms, for example chosen from undecanal, dodecanal, tridecanal, tetradecanal, pentadecanal, hexadecanal, heptadecanal, octodecanal and the acetal. Preferably, the C11-C13 aliphatic aldehyde or the acetal thereof is a C12 aliphatic aldehyde or the acetal thereof, for example a dodecanal or the acetal thereof.

The expression "the acetal thereof" or "their acetal(s)" as used herein covers the di-alkyl acetal of the corresponding C11-C18 aliphatic aldehyde. More particularly, the di-methyl or di-ethyl acetals of the C11-C18 aliphatic aldehyde are preferred.

According to an embodiment, the acetalization or trans-acetalization step may be conducted with or without solvent. When the reaction is conducted in the presence of a solvent, the solvent is preferably a polar solvent.

Typically, the solvent may be chosen from dimethylformamide (DMF), dimethylsulfoxide (DMSO), dimethylacetamide (DMA), acetonitrile ($CH_3CN$), tetrahydrofuran (THF), 2-methyltetrahydrofuran (2Me-THF), cyclopentyl methyl ether (CPME), methanol (MeOH), ethanol (EtOH), propanol (PrOH), isopropanol (iPrOH), butanol (BuOH), dibutyl ether (DBE), methyl tert-butyl ether (MTBE) and trimethoxypropane (TMP).

In-depth experimental work led to a selection of conditions that allow observation of conversion rates and optimal yields during acetalization or trans-acetalization steps. Better results were obtained when the molar ratio [(C11-C18 aliphatic aldehyde or their acetal):monosaccharide] is between 5:1 and 1:5, preferably between 4:1 and 1:4, and advantageously between 3:1 and 1:3.

The inventors have more particularly shown that, during an acetalization reaction, the molar ratio of C11-C18 aliphatic aldehyde:monosaccharide comprised between 1:1 and 1:5, preferably between 1:1 and 1:4, and in a preferred manner between 1:3 and 1:2 improves the yields and conversion rates.

The inventors have additionally shown that, during trans-acetalization reactions, a molar ratio of C11-C18 aliphatic aldehyde:monosaccharide comprised between 1:1 and 5:1, preferably between 5:4 and 4:1, and preferably between 3:1 and 4:3, preferably between 3:2 and 2:5 improves the yields and conversion rates. The catalysts used are the same as those of the acetalization reaction.

Such a process may additionally comprise at least one neutralization and/or filtration and/or purification step after any one of the dehydration, if need be, acetalization or trans-acetalization steps.

When a purification step is provided, said purification step may be for example a crystallization, a recrystallization or a chromatography. Preferably, chromatography is conducted using a non-aqueous polar solvent. In general, when a filtration and/or purification step is provided before the hydrogenolysis step, the non-aqueous polar solvent may be the same as that used during the hydrogenolysis step.

Advantageously, the hydrogenolysis step is conducted at a temperature comprised between 80° C. and 140° C., and/or at a hydrogen pressure comprised between 15 and 50 bar, preferably between 20 and 40 bar.

The hydrogenolysis step is conducted advantageously in a polar aprotic solvent, preferably a non-aqueous solvent. In fact, aprotic solvents provide better conversion. Examples of aprotic solvents are, among others, without limitation, alkanes, 1,2,3-trimethoxypropane (TMP), methyl tert-butyl ether (MTBE), tetrahydrofuran (THF), 2-methyl tetrahydrofuran (2Me-THF), dibutyl ether (DBE) and cyclopentyl methyl ether (CPME). Preferably, the aprotic solvent is CPME. Alkanes are advantageous because they allow better hydrogen solubilization in the medium. However, the conversion is lower than for other aprotic solvents such as CPME. Generally, among alkanes, dodecane and heptane are preferred.

The hydrogenolysis step is conducted preferably in a polar aprotic solvent at a temperature comprised between 80° C. and 140° C., and/or at a hydrogen pressure comprised between 15 and 50 bar, in the presence of a catalyst suitable for hydrogenolysis reactions.

Preferably, the hydrogenolysis step is conducted in a non-aqueous polar solvent at a temperature comprised between 100° C. and 130° C. and/or at a pressure comprised between 25 and 35 bar.

Generally, the hydrogenolysis is conducted in the presence of a suitable catalyst such as a catalyst containing precious metals or common metals. More particularly, the common metals may be iron or non-iron metals. Typically, hydrogenolysis is conducted in the presence of a catalyst containing iron metals.

As an indication, a metal catalyst belonging to the group of iron metals may be nickel, cobalt or iron.

Preferably, hydrogenolysis is conducted using a catalyst containing precious metals such as palladium, rhodium, ruthenium, platinum or iridium.

As a general rule, the catalyst used during hydrogenolysis may be fixed on a substrate such as carbon, alumina, zirconia or silica or any mixture of these. Such a substrate is for example a bead. Accordingly, a palladium catalyst fixed on carbon beads (Pd/C) may be advantageously used. These catalysts may be doped by adding precious metals or common metals. These are called doping agents. Typically, the doping agent represents 1 to 10% by weight of the catalyst.

Typically, the composition is bactericidal or bacteriostatic for Gram-positive bacteria.

Advantageously, the bactericidal or bacteriostatic composition is incorporated in a food, cosmetic, pharmaceutical, phytosanitary, veterinary or surface treatment composition. Such as, for example, a cosmetic and/or dermatological composition for cleansing and/or treating skin, particularly in the form of a cream, a gel, a powder, a lotion, a butter in particular, a shower gel, soap, shampoo, shower bath, deodorant, antiperspirant, moist wipe, sun protection formulation or decorative cosmetic formulation.

A bactericidal or bacteriostatic composition as described may be used as a hygiene or dermatological product for external use.

Typically a "hygiene product" refers to any product used for cleansing, disinfection or hygiene, including for example a lotion, mousse, spray or liquid but also wipes or any substrate that can be impregnated with the composition according to the invention. The expression "dermatological product" refers to any product intended for application on the skin or mucous membranes.

Use in the Treatment or Prevention of a Gram-positive Bacterial Infection.

A composition as described may be used in the treatment or prevention of bacterial infections by Gram-positive bacteria.

"Treatment" is understood to mean curative treatment (aiming to at least reduce, eradicate or stop the development of the infection) in a patient. "Prevention" is understood to mean prophylactic treatment (aiming to reduce the risk of the infection appearing) in a patient.

The "patient" may be, for example, a human being or a non-human mammal (for example a rodent (mouse, rat), a feline, a dog or a primate) affected by or that could be affected by bacterial infections and in particular Gram-positive bacterial infections. Preferably, the subject is a human.

The expression "Gram-positive" refers to bacteria that are colored dark blue or purple by the Gram stain, by contrast with Gram-negative bacteria that cannot retain the purple stain. The Gram staining technique uses bacteria's membrane and wall characteristics.

Typically, the Gram-positive bacteria are bacteria from the phylum of Firmicutes, typically of the class of Bacilli in particular chosen from bacteria of the order of Lactobacillales or Bacillales.

According to one embodiment of the invention, bacteria from the order of Bacillales are chosen from the family of Alicyclobacillaceae, Bacillaceae, Caryophanaceae, Listeriaceae, Paenibacillaceae, Pasteuriaceae, Planococcaceae, Sporolactobacillaceae, Staphylococcaceae, Thermoactinomycetacea and Turicibacteraceae.

Typically, bacteria from the Listeriaceae family are for example from the genus *Brochothrix* or *Listeria* and may be typically chosen from *L. fleischmannii, L. grayi, L. innocua, L. ivanovii, L. marthii, L. monocytogenes, L. rocourtiae, L. seeligeri, L. weihenstephanensis* and *L. welshimeri.*

When Gram-positive bacteria are bacteria from the Staphylococcaceae family, they are in particular chosen from bacteria from the genus *Staphylococcus, Gemella, Jeotgalicoccus, Macrococcus, Salinicoccus* and *Nosocomiicoccus.*

Bacteria from the genus *Staphylococcus* for example chosen from *S. arlettae, S. agnetis, S. aureus, S. auricularis, S. capitis, S. caprae, S. carnosus, S. caseolyticus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri* and *S. xylosus.*

According to another embodiment of the invention, bacteria from the order of Lactobacillales are chosen from a family of Aerococcaceae, Carnobacteriaceae, Enterococcaceae, Lactobacillaceae, Leuconostocaceae and Streptococcaceae.

Typically, bacteria from the family of Enterococcaceae are chosen from bacteria from the genus *Bavariicoccus, Catellicoccus, Enterococcus, Melissococcus, Pilibacter, Tetragenococcus, Vagococcus.*

Bacteria from the genus *Enterococcus* are chosen for example from *E. malodoratus, E. avium, E. durans, E.*

*faecalis, E. faecium, E. gallinarum, E. hirae, E. solitarius,* preferentially *E. avium, E. durans, E. faecalis* and *E. faecium.*

Bacteria from the genus *Staphylococcus* and more particularly *S. aureus* are responsible for many infections of the skin or mucous membranes such as vaginal or nasal membranes. For example, infections such as folliculitis, abscesses, paronychia, boils, impetigo, infections between the digits, anthrax (staphylococcal anthrax), cellulitis, secondary wound infections, otitis, sinusitis, hidradenitis, infectious mastitis, post-traumatic skin infections or infections on burnt skin.

Bacteria from the genus *Enterococcus* and in particular *E. faecalis* are responsible in particular for endocarditis, and infections of the bladder, prostate and epididymis.

A method for treatment or prevention of a bacterial infection by Gram-positive bacteria, preferentially an infection of the skin or mucous membranes, by administration, preferentially topical, to an individual who needs it, of a therapeutically effective quantity of the composition described.

In a person infected by a Gram-positive bacterium, "therapeutically effective quantity" is understood to mean sufficient quantity to prevent the infection from changing for the worse, or sufficient to make the infection regress. In a person who is not infected, the "therapeutically effective quantity" is the quantity that is sufficient to protect a person who would come into contact with a Gram-positive bacterium and prevent the occurrence of the infection caused by this Gram-positive bacterium.

Typically, topical administration is done by applying the composition according to the invention to the skin or mucous membranes.

Method for Disinfection or Prevention of Bacterial Colonization of a Substrate

A method for disinfection or prevention of bacterial colonization by Gram-positive bacteria of a substrate comprises putting the substrate into contact with a described composition.

Typically, the substrate is any substrate that can be colonized by Gram-positive bacteria and that can transmit the infection to an animal by contact or ingestion.

For example, the substrate may be a food of plant or animal origin or a food composition comprising such foods or an extract of these foods and in particular cereals, fruits, vegetables, meat, fish or offal.

The substrate may also be one or more elements selected from among metals, plastics, glass, concrete or stone.

Preferentially the substrate is a utensil, a tool or a device used in the food industry (cooking utensils, a container, a cold storage system, a refrigerator, cold rooms, etc.), in a hospital environment, such as for example surgical tools or prostheses, or for public transit (hand rails, seats, etc.).

A composition for disinfection, cleaning, sterilization or purification of surfaces.

Although having distinct meanings, the terms "comprising", "containing", "including" and "consisting of" have been used interchangeably in the description of the invention, and may be replaced by each other.

The invention will be better understood upon reading the following figures and examples given only as examples.

EXAMPLES

The sorbitan acetals were prepared by acetalization or trans-acetalization of sugars following the procedure previously described in patent No. 13/01375 "Method for preparing long-chain alkyl cyclic acetals made from sugars." The sugar acetals are then reduced using reduction conditions without an acid catalyst previously described in patent No. 14/01346. For indication, the synthesis of sorbitan acetals and ethers is described below.

Example 1

General Procedure for the Synthesis of Sorbitan Acetals (A)

Sorbitol Dehydration:

D-sorbitol (20 g, 110 mmol) and 0.1 mol % of camphorsulfonic acid are added to a 150-mL stainless-steel autoclave. The reactor is hermetically sealed, purged three times with hydrogen then hydrogen was introduced until the pressure reached 50 bar. The system is then heated to 140° C. and stirred with a mechanical stirrer for 15 hours. After cooling to room temperature, the hydrogen pressure was released and the crude reaction mixture was diluted in ethanol (200 mL) to produce a homogeneous yellow mixture. The solvent is evaporated under low pressure and the residue is then crystallized from cold methanol and filtered under vacuum. The crystalline material was washed with cold methanol to give 1,4-sorbitan (5.88 g, 35% of theory) in the form of a white solid. The purity is >98%, as determined by HPLC, while the crystals had a melting point of 113-114° C. The degree of reaction conversion was determined at 73%, by which a mixture of sorbitol, 1,4-sorbitan, isosorbide and a few by-products in very small quantities were obtained, such that the ratio of 1,4-sorbitan: isosorbide was determined as being 80:20.

General Procedure for Sorbitan Acetalization

In a round-bottomed flask equipped with a condenser and a $CaCl_2$ trap, under an argon atmosphere, 1,4-D-sorbitan (5.00 g, 30.5 mmol, 3 equiv) is dissolved in dry ethanol (15 mL). The aldehyde (10.2 mmol, 1 equiv) is then added dropwise followed by the camphorsulfonic acid (CSA, 10% by mass relative to the aldehyde). The reaction mixture was held at 80° C. for 15 hours with magnetic stirring. The reaction mixture is cooled and the solvent is evaporated under low pressure. The residue is triturated in ethyl acetate and the excess sorbitan is removed by filtration and washed with cold ethyl acetate. This operation may be repeated to remove any traces of sorbitan. The filtrate was concentrated under low pressure. The residue is purified by chromatography on a silica gel column to give the sorbitan alkyl acetals. The composition of the mixture of regioisomers 5,6-O-alkylidene- and 3,5-O-alkylidene-1,4-D-sorbitan was determined by HPLC. In addition, each regioisomer was obtained in the form of a mixture of two diastereoisomers.

Procedure for Sorbitan Trans-Acetalization:

In a round-bottomed flask, 1,4-sorbitan (0.5 g, 3 mmol) was dissolved in ethanol (7.5 mL) and 1,1-diethoxypentane (1.15 mL, 6 mmol) was added under an argon flow, then camphorsulfonic acid (50 mg; 10% w/w). The reaction mixture is heated to 80° C. with magnetic stirring. After 3 hours, the mixture was neutralized and concentrated under low pressure. The residue was purified by flash chromatography (ethyl acetate/cyclohexane 80:20 to 100:0) to give the sorbitan acetal (0.43 g, 66% isolated yield) in the form of a colorless oil. HPLC revealed a mixture of 4 isomers.

Example 1a

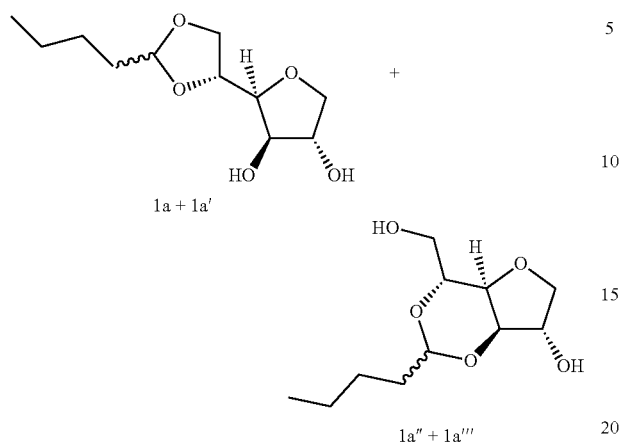

1a + 1a'

1a" + 1a"'

5,6-O-Pentylidene-1,4-D-sorbitan 1a and 1a' and 3,5-O-pentylidene-1,4-D-sorbitan 1a" and 1a"': The compounds were obtained from 1,4-D-sorbitan (0.49 g, 3 mmol) and valeraldehyde (0.107 mL, 1 mmol) according to the general procedure (A). After reaction, the residue is purified by chromatography on silica gel column (EtOAc/cyclohexane 80:20→100:0) to give a 43:57 mixture of sorbitan acetal regioisomers in the 5,6-O- and 3,5-O- positions (0.189 g, 81%) in the form of a colorless oil. The product obtained is a mixture of 5,6-O- and 3,5-O- sorbitan acetal regioisomers, and each regioisomer is a mixture of diastereoisomers (26:17:47:10) as determined by HPLC. NMR $^1$H (300 MHz, $d_6$-DMSO) $\delta_H$ for all the isomers: 0.85 (3H, t, J=7.2), 1.16-1.35 (4H, m), 1.35-1.60 (2H, m), 3.30-4.30 (8H, sorbitan protons), 4.67-5.33 (3H, 3m, 1H acetal and 2 OH); NMR $^{13}$C (75 MHz, $d_6$-DMSO) $\delta_C$ for the 5,6-O-regioisomers 1a and 1a': 13.90 ($CH_3$), 22.06 ($CH_2$), 25.68 and 25.81 ($CH_2$), 33.16 ($CH_2$), 66.59 and 66.93 ($CH_2$), 72.79 and 73.19 (CH), 73.43 ($CH_2$), 75.46 and 75.68 (CH), 76.55 and 76.61 (CH), 80.74 and 81.01 (CH), 103.29 and 103.37 (CH); $\delta_C$ for the 3,5-O-regioisomers 1" and 1a"': 13.92 and 13.93 ($CH_3$), 21.95 and 22.00 ($CH_2$), 25.53 and 25.75 ($CH_2$), 33.73 and 34.13 ($CH_2$), 60.78 and 61.92 ($CH_2$), 72.37 and 73.55 ($CH_2$), 72.58 and 72.99 (CH), 73.19 and 73.96 (CH), 74.87 and 76.45 (CH), 78.38 and 79.08 (CH), 93.83 and 96.06 (CH); IR v max: 3386 (OH), 2954, 2873, 1716, 1412, 1145, 1461, 1061, 1029, 967; HRMS (ESI$^+$) calculated $C_{11}H_{20}NaO_5$: 255.1208 [M+Na]$^+$; measured: 255.1203 (+1.8 ppm); HPLC (isocratic 80:20 $H_2O$/$CH_3CN$+0.1% $H_3PO_4$): $R_t$ for the 3,5-O-regioisomers=9.70 min (1a", 47%) and 11.25 min (1a"', 10%); $R_t$ for the 5,6-O-regioisomers=12.50 min (1a, 26%) and 14.49 (1a', 17%).

Example 1b

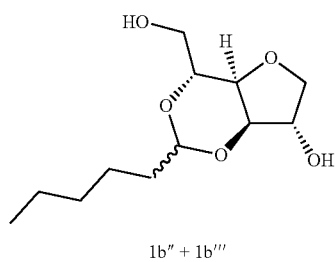

1b" + 1b"'

5,6-O-Hexylidene-1,4-D-sorbitan 1b and 1b' and 3,5-O-hexylidene-1,4-D-sorbitan 1b" and 1b"': The compounds were obtained from 1,4-D-sorbitan (0.49 g, 3 mmol) and hexanal (0.124 mL, 1 mmol) according to the general procedure (A). After reaction, the residue is purified by chromatography on silica gel column (EtOAc/cyclohexane 80:20→100:0) to give a 57:43 mixture of sorbitan acetal regioisomers in the 5,6-O- and 3,5-O- positions (0.144 g, 58%) in the form of a yellow oil. The product obtained is a mixture of 5,6-O- and 3,5-O- sorbitan acetal regioisomers, and each regioisomer is a mixture of diastereoisomers (32:25:31:12) as determined by HPLC. NMR $^1$H (300 MHz, $d_6$-DMSO) $\delta_H$ for all the isomers: 0.85 (3H, t, J=6.5), 1.12-1.40 (6H, m), 1.45-1.58 (2H, m), 3.30-4.30 (8H, m, sorbitan protons), 4.72-4.90 (1H, m, acetal proton), 5.07-5.28 (2H, 2m, OH); NMR $^{13}$C (75 MHz, $d_6$-DMSO) $\delta_C$ for the 5,6-O- regioisomers 1b and 1b': 13.91 ($CH_3$), 22.12 ($CH_2$), 23.24 and 23.38 ($CH_2$), 31.24 ($CH_2$), 33.50 ($CH_2$), 66.64 and 66.98 ($CH_2$), 72.86 and 73.24 (CH), 73.48 ($CH_2$), 75.50 and 75.73 (CH), 76.60 and 76.66 (CH), 80.78 and 81.06 (CH), 103.34 and 103.42 (CH); $\delta_C$ for the 3,5-O-regioisomers 1b" and 1b"': 13.93 ($CH_3$), 22.12 ($CH_2$), 23.09 and 23.31 ($CH_2$), 31.17 ($CH_2$), 34.06 and 34.48 ($CH_2$), 60.85 and 61.97 ($CH_2$), 72.42 and 73.61 ($CH_2$), 72.64 and 72.86 (CH), 73.08 and 74.01 (CH), 74.94 and 76.48 (CH), 78.40 and 79.13 (CH), 93.90 and 96.13 (CH); IR v max: 3386 (OH), 2929 ($CH_3$), 2871 ($CH_2$), 2360, 2341, 1465, 1407, 1143, 1034; HRMS (ESI$^+$): [M+Na]$^+$ $C_{12}H_{22}NaO_5$ calculated 269.1359, measured 269.1360 (−0.4 ppm); HPLC (isocratic 80:20 $H_2O$/$CH_3CN$+0.1% $H_3PO_4$): $R_t$ for the 3,5-O- regioisomers=20.77 min (1b', 31%) and 24.65 min (1b"', 12%); $R_t$ for the 5,6-O- regioisomers=28.28 min (1b, 32%) and 33.90 (1b', 25%).

Example 1c

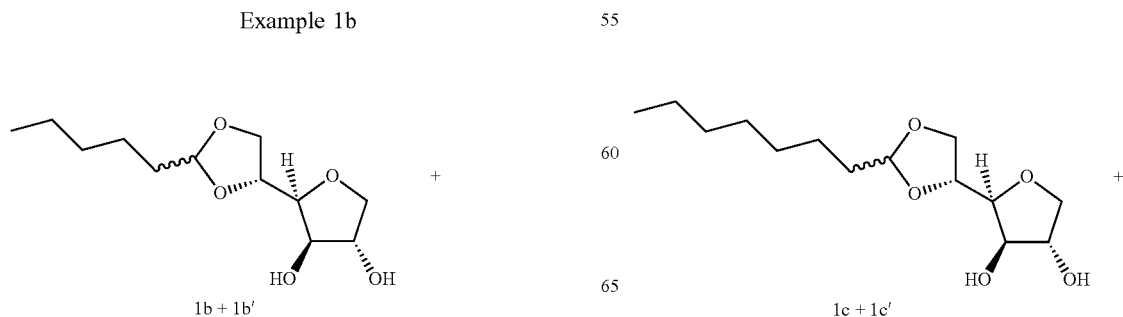

1c + 1c'

13

-continued

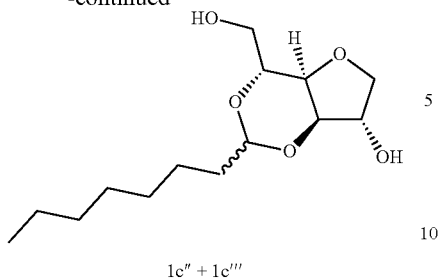

1c″ + 1c‴

5,6-O-Octylidene-1,4-D-sorbitan 1c and 1c′ and 3,5-O-octylidene-1,4-D-sorbitan 1c″ and 1c‴: The compounds were obtained from 1,4-D-sorbitan (1.00 g, 6 mmol) and octanal (0.317 mL, 2 mmol) according to the general procedure (A). After reaction, the residue is purified by chromatography on silica gel column (EtOAc/cyclohexane 60:40→100:0) to give a 61:39 mixture of sorbitan acetal regioisomers in the 5,6-O- and 3,5-O- positions (0.102 g, 37%) in the form of a white paste. The product obtained is a mixture of 5,6-O- and 3,5-O- sorbitan acetal regioisomers, and each regioisomer is a mixture of diastereoisomers (32:29:28:11) as determined by HPLC. NMR $^1$H (300 MHz, d$_6$-DMSO) $\delta_H$ for all the isomers: 0.86 (3H, t, J=8.7), 1.10-1.42 (10H, m), 1.43-1.62 (2H, m), 3.38-4.31 (8H, m, sorbitan protons), 4.70-4.90 (1H, m, acetal proton), 5.02-5.28 (2H, 2m, OH); NMR $^{13}$C (75 MHz, d$_6$-DMSO) $\delta_C$ for the 5,6-O- regioisomers 1c and 1c′: 13.96 (CH$_3$), 22.13 (CH$_2$), 23.40 and 23.58 (CH$_2$), 28.72 (2 CH$_2$), 31.26 (CH$_2$), 33.54 (CH$_2$), 66.22 and 66.96 (CH$_2$), 72.85 and 73.24 (CH), 73.47 (CH$_2$), 75.49 and 75.72 (CH), 76.59 and 76.64 (CH), 80.77 and 81.05 (CH), 103.31 and 103.40 (CH); $\delta_C$ for the 3,5-O- regioisomers 1c″ and 1c‴: 13.96 (CH$_3$), 22.13 (CH$_2$), 23.62 and 23.70 (CH$_2$), 28.92 and 28.99 (2 CH$_2$), 31.26 (CH$_2$), 34.09 and 34.51 (CH$_2$), 60.85 and 61.95 (CH$_2$), 72.42 and 73.60 (CH$_2$), 72.62 and 72.90 (CH), 73.10 and 73.99 (CH), 74.93 and 76.46 (CH), 78.36 and 79.10 (CH), 93.88 and 96.09 (CH); IR ν max: 3425 (OH), 2953 (CH$_3$), 2920 (CH$_2$), 2855, 1467, 1414, 1257, 1047; HRMS (ESI$^+$): [M+Na]$^+$ C$_{14}$H$_{26}$NaO$_5$ calculated 297.1672, measured 297.1670 (+1.0 ppm); HPLC (isocratic 60:40 H$_2$O/CH$_3$CN+ 0.1% H$_3$PO$_4$): R$_t$ for the 3,5-O- regioisomers=11.50 min (1c′, 28%) and 12.93 min (1c‴, 11%); R$_t$ for the 5,6-O- regioisomers=14.83 min (1c, 32%) and 16.56 (1c′, 29%).

Example 1d

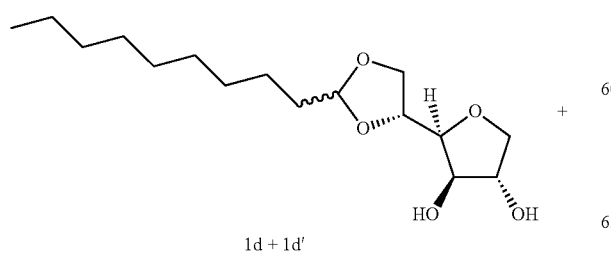

1d + 1d′

14

-continued

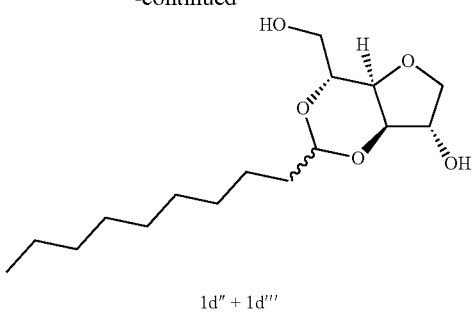

1d″ + 1d‴

5,6-O-Decylidene-1,4-D-sorbitan 1d and 1d′ and 3,5-O-decylidene-1,4-D-sorbitan 1d′ and 1d‴: The compounds were obtained from 1,4-D-sorbitan (1.00 g, 6 mmol) and decanal (0.382 mL, 2 mmol) according to the general procedure (A). After reaction, the residue is purified by chromatography on silica gel column (EtOAc/cyclohexane 50:50→80:20) to give a 64:36 mixture of sorbitan acetal regioisomers in the 5,6-O- and 3,5-O- positions (0.098 g, 32%) in the form of a white solid (Melting point=72° C.). The product obtained is a mixture of 5,6-O- and 3,5-O- sorbitan acetal regioisomers, and each regioisomer is a mixture of diastereoisomers (35:29:25:11) as determined by HPLC. NMR $^1$H (300 MHz, CDCl$_3$) $\delta_H$ for all the isomers: 0.85 (3H, t, J=6.9), 1.10-1.45 (14H, m), 1.47-1.70 (2H, m), 3.45 (2H, br s, OH protons), 3.60-4.39 (8H, m, sorbitan protons), 4.75 (t, 29% H acetal, J=5.1), 4.83 (t, 11% H acetal, J=4.8), 4.85 (t, 35% H acetal, J=5.3), 4.97 (t, 26% H acetal, J=4.8); NMR $^{13}$C (75 MHz, CDCl$_3$) $\delta_C$ for the 5,6-O- regioisomers 1d and 1d′: 14.19 (CH$_3$), 22.76 (CH$_2$), 24.12 and 24.17 (CH$_2$), 29.40 (CH$_2$), 29.63 (3 CH$_2$), 31.97 (CH$_2$), 33.98 and 34.12 (CH$_2$), 68.17 and 68.57 (CH$_2$), 73.57 and 73.66 (CH), 73.77 and 74.13 (CH$_2$), 75.51 and 75.91 (CH), 77.30 and 77.56 (CH), 79.64 and 81.15 (CH), 104.99 and 105.14 (CH); $\delta_C$ for the 3,5-O- regioisomers 1d″ and 1d‴: 14.19 (CH$_3$), 22.76 (CH$_2$), 23.84 and 24.12 (CH$_2$), 29.40 (CH$_2$), 29.63 (3 CH$_2$), 31.97 (CH$_2$), 34.19 and 34.83 (CH$_2$), 61.76 and 63.41 (CH$_2$), 72.80 and 73.14 (CH), 73.81 (CH$_2$), 75.15 and 75.34 (CH), 77.25 and 77.90 (CH), 81.37 (CH), 95.73 and 97.92 (CH); IR ν max: 3433 (OH), 2918 (CH$_3$), 2851 (CH$_2$), 1739, 1123, 1080, 1048; HRMS (ESI): [M+Na]$^+$ C$_{16}$H$_{30}$NaO$_5$ calculated 325.1985, measured 325.1991 (−1.7 ppm); HPLC (isocratic 50:50 H$_2$O/CH$_3$CN+ 0.1% H$_3$PO$_4$): R$_t$ for the 3,5-O- isomers=11.97 min (1d″, 25%) and 13.27 min (1d′, 11%); R$_t$ for the 5,6-O- regioisomers=15.21 min (1d, 35%) and 16.60 (1d′, 29%).

Example 1e

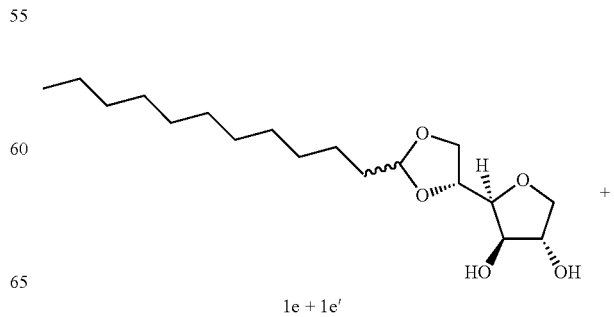

1e + 1e′

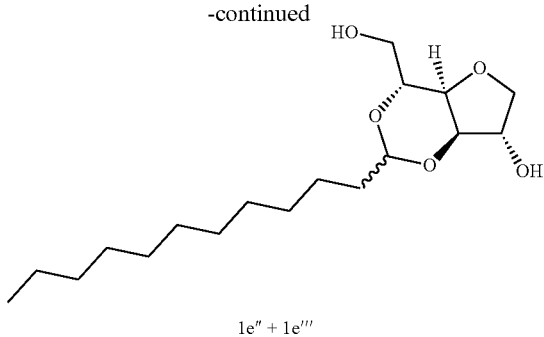

1e'' + 1e'''

5,6-O-Dodecylidene-1,4-D-sorbitan 1e and 1e' and 3,5-O-dodecylidene-1,4-D-sorbitan 1e'' and 1e''': The compounds were obtained from 1,4-D-sorbitan (1.00 g, 6 mmol) and dodecanal (0.450 mL, 2 mmol) according to the general procedure (A). After reaction, the residue is purified by chromatography on silica gel column (EtOAc/cyclohexane 50:50→70:30) to give a 48:52 mixture of sorbitan acetal regioisomers in the 5,6-O- and 3,5-O- positions (0.095 g, 29%) in the form of a white solid (Melting point=82° C.). The product obtained is a mixture of 5,6-O- and 3,5-O-sorbitan acetal regioisomers, and each regioisomer is a mixture of diastereoisomers (25:23:40:12) as determined by HPLC. NMR $^1$H (300 MHz, d$_6$-DMSO) $\delta_H$ for all the isomers: 0.85 (3H, t, J=6.9), 1.12-1.42 (18H, m), 1.43-1.59 (2H, m), 3.41-4.30 (8H, m, sorbitan protons), 4.72-4.89 (1H, m, acetal proton), 5.00-5.12 and 5.17-5.33 (2H, 2m, OH protons); NMR $^{13}$C (75 MHz, d$_6$-DMSO) $\delta_C$ for the 5,6-O-regioisomers 1e and 1e': 13.95 (CH$_3$), 22.15 (CH$_2$), 23.60 and 23.69 (CH$_2$), 28.79 (CH$_2$), 28.93 (CH$_2$), 29.05 (CH$_2$), 29.07 (CH$_2$), 29.08 (CH$_2$), 29.10 (CH$_2$), 31.37 (CH$_2$), 33.54 (CH$_2$), 66.59 and 66.93 (CH$_2$), 72.87 and 73.26 (CH), 73.46 (CH$_2$), 75.49 and 75.72 (CH), 76.58 and 76.63 (CH), 80.75 and 81.04 (CH), 103.29 and 103.38 (CH); $\delta_C$ for the 3,5-O-regioisomers 1e'' and 1e''': 13.95 (CH$_3$), 22.15 (CH$_2$), 23.38 and 23.60 (CH$_2$), 28.79 (CH$_2$), 28.93 (CH$_2$), 29.05 (CH$_2$), 29.07 (CH$_2$), 29.08 (CH$_2$), 29.10 (CH$_2$), 31.37 (CH$_2$), 34.10 and 34.51 (CH$_2$), 60.84 and 61.94 (CH$_2$), 72.60 and 72.95 (CH), 72.43 and 73.59 (CH$_2$), 73.17 and 73.98 (CH), 74.92 and 76.43 (CH), 78.31 and 79.07 (CH), 93.87 and 96.06 (CH); IR ν max: 3412 (OH), 2917 (CH$_3$), 2849 (CH$_2$), 1468, 1418, 1256, 1082, 1050; HRMS (ESI$^+$): [M+Na]$^+$ C$_{18}$H$_{34}$NaO$_5$ calculated 353.2298, measured 353.2300 (−0.3 ppm); HPLC (isocratic 50:50 H$_2$O/CH$_3$CN+ 0.1% H$_3$PO$_4$): R$_t$ for the 3,5-O-regioisomers=31.89 min (1e', 40%) and 35.77 min (1e''', 12%); R$_t$ for the 5,6-O-regioisomers=41.72 min (1e, 25%) and 46.18 (1e', 23%).

Example 2

General Procedure for the Synthesis of a Sorbitan Ether (B)

In a 300-mL stainless-steel autoclave, the mixture of regioisomers and diastereoisomers of 1,4-D-sorbitan acetals (20 mmol) is diluted in cyclopentyl methyl ether (CPME, 200 mL) and 5%-Pd/C (1.00 g, 5 mol % palladium) is added. The reactor is hermetically sealed, purged three times with hydrogen then hydrogen is introduced to a pressure of 30 bar. The reaction mixture is stirred mechanically and heated to 120° C. for 15 hours. After returning to ambient temperature, the hydrogen pressure is released and the reaction mixture is diluted in absolute ethanol (EtOH, 100 mL) and filtered (Millipore Durapore 0.01 μm filter). The filtrate is concentrated under low pressure to give the mixture of sorbitan ether regioisomers.

Example 2

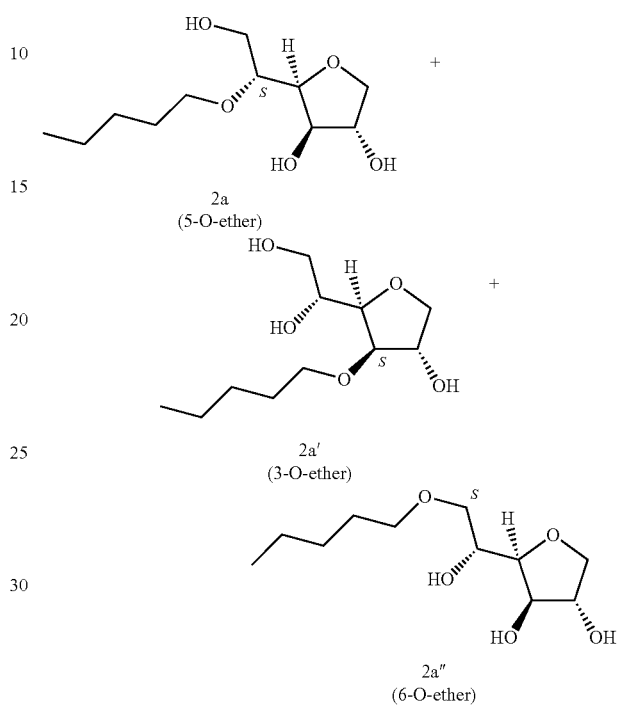

2a (5-O-ether)

2a' (3-O-ether)

2a'' (6-O-ether)

Pentyl-1,4-D-sorbitan 2a, 2a' and 2a'': The compounds were obtained from the 43:57 mixture of 5,6-O-pentylidene-1,4-D-sorbitan 1a and 1a' and 3,5-O-pentylidene-1,4-D-sorbitan 1a'' and 1a''' (0.98 g, 4.22 mmol) according to the general procedure (B). After reaction, the residue is purified by chromatography on silica gel column (EtOAc/cyclohexane, 90:10→100:0 then EtOH/EtOAc 10:90) to give a mixture of sorbitan ether regioisomers 2a, 2a' and 2a'' (0.686 g, 69%) in the form of a white paste. The product is a 26:33:41 mixture of 5-O-pentyl-2a, 3-O-pentyl-2a' and 6-O-pentyl-1,4-D-sorbitan 2a'' as determined by HPLC. NMR $^1$H (300 MHz, d$_6$-DMSO) $\delta_H$ for all the isomers: 0.86 (3H, t, J=6.9), 1.19-1.35 (4H, m), 1.39-1.56 (2H, m), 3.22-3.99 and 4.05-4.11 (10H, m, sorbitan protons+OCH$_2$ ethers), $\delta_H$ for isomer 2a: 4.31 (1H, t, J=5.8, OH$^6$), 4.84 (1H, d, J=4.3, OH$^3$), 5.00 (1H, d, J=2.9, OH$^2$), $\delta_H$ for isomer 2a' 14b: 4.31 (1H, t, J=5.2, OH$^6$), 4.37 (1H, d, J=5.4, OH$^5$), 5.06 (1H, d, J=3.3, OH$^2$), $\delta_H$ for isomer 2a'': 4.55 (1H, d, J=5.8, OH$^5$), 4.82 (1H, d, J=4.3, OH$^3$), 4.99 (1H, d, J=2.8, OH$^2$); NMR $^{13}$C (75 MHz, d$_6$-DMSO) $\delta_C$ for minor isomer (26%) 2a: 14.03 (CH$_3$), 22.06 (CH$_2$), 27.88 (CH$_2$), 29.55 (CH$_2$), 62.02 (CH$_2$), 69.79 (CH$_2$), 73.15 (CH$_2$), 75.53 (CH), 76.46 (CH), 77.38 (CH), 79.29 (CH); $\delta_C$ for intermediate isomer (33%) 2a': 13.99 (CH$_3$), 22.03 (CH$_2$), 27.91 (CH$_2$), 29.22 (CH$_2$), 64.20 (CH$_2$), 68.72 (CH), 69.52 (CH$_2$), 73.23 (CH), 73.61 (CH$_2$), 80.10 (CH), 83.96 (CH); $\delta_C$ for major isomer (41%) 2a'': 13.99 (CH$_3$), 22.02 (CH$_2$), 27.87 (CH$_2$), 28.99 (CH$_2$), 67.50 (CH), 70.60 (CH$_2$), 73.36 (CH$_2$), 73.49 (CH$_2$), 75.66 (CH), 76.38 (CH), 80.34 (CH); HRMS (ESI$^+$): [M+Na]$^+$ C$_{11}$H$_{22}$NaO$_5$ calculated 257.1359, measured 257.1363 (−1.4 ppm); HPLC (C18 column, isocratic 80:20 H$_2$O/CH$_3$CN+ 0.1% H$_3$PO$_4$): R$_t$ 7.20 min (2a, 26%), 9.25 min (2a', 33%) and 10.79 min (2a", 41%).

Example 2b

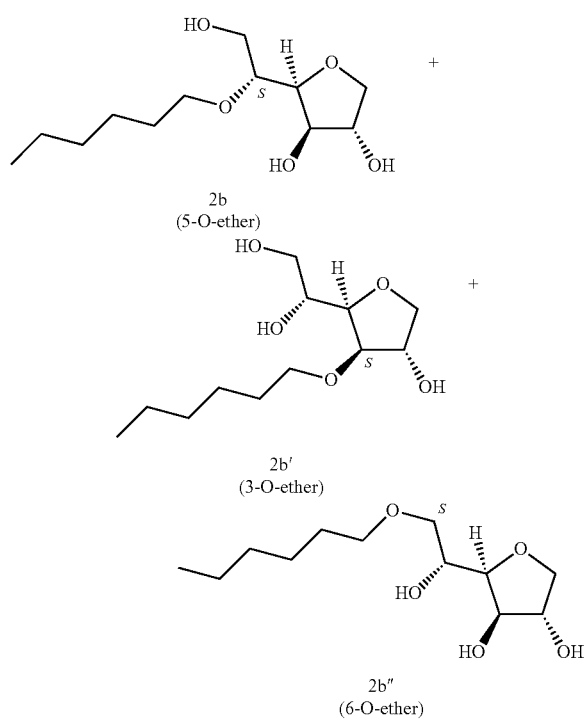

2b
(5-O-ether)

2b'
(3-O-ether)

2b"
(6-O-ether)

Hexyl-1,4-D-sorbitan 2b, 2b' and 2b": The compounds were obtained from the 57:43 mixture of 5,6-O-hexylidene-1,4-D-sorbitan 1b and 1b' and 3,5-O-hexylidene-1,4-D-sorbitan 1b" and 1b'" (4.92 g, 20.0 mmol) according to the general procedure (B). After reaction, the residue is purified by chromatography on silica gel column (EtOAc/cyclohexane, 80:20→100:0 then EtOH/EtOAc 10:90) to give a mixture of sorbitan ether regioisomers 2b, 2b' and 2b" (3.25 g, 65%) in the form of a white paste. The product is a 33:16:51 mixture of 5-O-hexyl-2b, 3-O-hexyl-2b' and 6-O-hexyl-1,4-D-sorbitan 2b" as determined by HPLC. NMR $^1$H (300 MHz, d$_6$-DMSO) δ$_H$ for all the isomers: 0.86 (3H, t, J=6.9), 1.16-1.36 (6H, m), 1.38-1.56 (2H, m), 3.25-4.00 and 4.05-4.11 (10H, m, sorbitan protons+OCH$_2$ ethers), δ$_H$ for isomer 2b: 4.31 (1H, t, J=5.5, OH$^6$), 4.83 (1H, d, J=4.4, OH$^3$), 4.99 (1H, d, J=2.9, OH$^2$), δ$_H$ for isomer 2b': 4.31 (1H, t, J=5.5, OH$^6$), 4.36 (1H, d, J=5.4, OH$^5$), 5.06 (1H, d, J=3.3, OH$^2$), δ$_H$ for isomer 2b": 4.54 (1H, d, J=5.8, OH$^5$), 4.81 (1H, d, J=4.3, OH$^3$), 4.99 (1H, d, J=2.9, OH$^2$); NMR $^{13}$C (75 MHz, d$_6$-DMSO) δ$_C$ for isomer 2b (33%): 14.00 (CH$_3$), 22.14 (CH$_2$), 25.36 (CH$_2$), 29.87 (CH$_2$), 31.27 (CH$_2$), 62.03 (CH$_2$), 69.84 (CH$_2$), 73.17 (CH$_2$), 75.57 (CH), 76.49 (CH), 77.40 (CH), 79.31 (CH); δ$_C$ for isomer 2b' (16%): 13.97 (CH$_3$), 22.17 (CH$_2$), 25.34 (CH$_2$), 29.52 (CH$_2$), 31.19 (CH$_2$), 64.21 (CH$_2$), 68.74 (CH), 69.56 (CH$_2$), 73.27 (CH), 73.62 (CH$_2$), 80.11 (CH), 83.98 (CH); δ$_C$ for isomer 2b" (51%): 13.97 (CH$_3$), 22.17 (CH$_2$), 25.40 (CH$_2$), 29.31 (CH$_2$), 31.23 (CH$_2$), 67.54 (CH$_2$), 70.65 (CH$_2$), 73.38 (CH$_2$), 73.50 (CH$_2$), 75.70 (CH), 76.40 (CH), 80.35 (CH); HRMS (ESI$^+$): [M+Na]$^+$ C$_{12}$H$_{24}$NaO$_5$ calculated 271.1516, measured 271.1521 (−1.7 ppm); HPLC (C18 column, isocratic 80:20 H$_2$O/CH$_3$CN+0.1% H$_3$PO$_4$): R$_t$ 17.49 min (2b, 33%), 24.45 min (2b', 16%) and 29.58 min (2b", 51%).

Example 2c

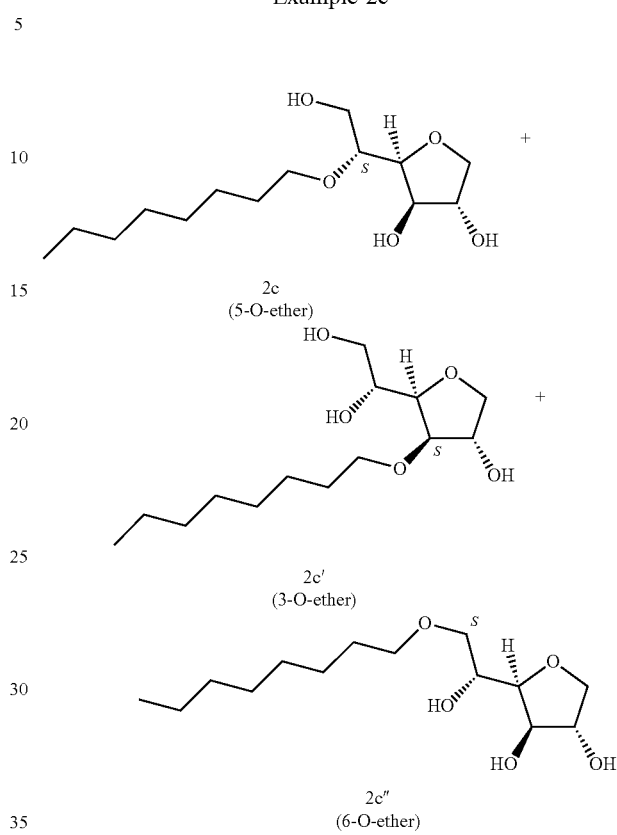

2c
(5-O-ether)

2c'
(3-O-ether)

2c"
(6-O-ether)

Octyl-1,4-D-sorbitan 2c, 2c' and 2c": The compounds were obtained from the 61:39 mixture of 5,6-O-octylidene-1,4-D-sorbitan 1c and 1c' and 3,5-O-octylidene-1,4-D-sorbitan 1c" and 1c'" (5.61 g, 20.4 mmol) according to the general procedure (B). After reaction, the residue is purified by chromatography on silica gel column (EtOAc/cyclohexane, 80:20→100:0 then EtOH/EtOAc 10:90) to give a mixture of sorbitan ether regioisomers 2c, 2c' and 2c" (4.79 g, 85%) in the form of a white solid. The product is a 33:22:45 mixture of 5-O-octyl-2c, 3-O-octyl-2c' and 6-O-octyl-1,4-D-sorbitan 2c" as determined by HPLC. NMR $^1$H (300 MHz, d$_6$-DMSO) δ$_H$ for all the isomers: 0.86 (3H, t, J=6.8), 1.13-1.35 (10H, m), 1.36-1.55 (2H, m), 3.27-3.99 and 4.05-4.11 (10H, m, sorbitan protons+OCH$_2$ ethers), δ$_H$ for isomer 2c: 4.31 (1H, t, J=5.8, OH$^6$), 4.84 (1H, d, J=4.5, OH$^3$), 5.00 (1H, d, J=2.8, OH$^2$), δ$_H$ for isomer 2c': 4.31 (1H, t, J=5.2, OH$^6$), 4.37 (1H, d, J=5.4, OH$^5$), 5.06 (1H, d, J=3.3, OH$^2$), δ$_H$ for isomer 2c": 4.54 (1H, d, J=5.8, OH$^5$), 4.81 (1H, d, J=4.3, OH$^3$), 4.99 (1H, d, J=2.8, OH$^2$); NMR $^{13}$C (75 MHz, d$_6$-DMSO): δ$_C$ for isomer 2c (33%): 13.98 (CH$_3$), 22.13 (CH$_2$), 25.66 (CH$_2$), 28.78 (CH$_2$), 28.99 (CH$_2$), 29.89 (CH$_2$), 31.32 (CH$_2$), 62.01 (CH$_2$), 69.83 (CH$_2$), 73.15 (CH$_2$), 75.53 (CH), 76.45 (CH), 77.38 (CH), 79.29 (CH); δ$_C$ for isomer 2c' (22%): 13.98 (CH$_3$), 22.13 (CH$_2$), 25.70 (CH$_2$), 28.75 (CH$_2$), 28.90 (CH$_2$), 29.53 (CH$_2$), 31.30 (CH$_2$), 64.18 (CH$_2$), 68.71 (CH), 69.52 (CH$_2$), 73.23 (CH), 73.60 (CH$_2$), 80.08 (CH), 83.95 (CH); δ$_C$ for isomer 2c" (45%): 13.98 (CH$_3$), 22.13 (CH$_2$), 25.70 (CH$_2$), 28.75 (CH$_2$), 28.93 (CH$_2$), 29.32 (CH$_2$), 31.30 (CH$_2$), 67.49 (CH), 70.61 (CH$_2$), 73.36 (CH$_2$), 73.49 (CH$_2$), 75.66 (CH), 76.37

(CH), 80.34 (CH); HRMS (ESI+): [M+Na]+ $C_{14}H_{28}NaO_5$ calculated 299.1829, measured 299.1832 (−1.2 ppm); HPLC (C18 column, isocratic 60:40 $H_2O/CH_3CN$+0.1% $H_3PO_4$): $R_t$ 8.79 min (2c, 33%), 9.80 min (2c', 22%) and 11.77 min (2c", 45%).

Example 2d

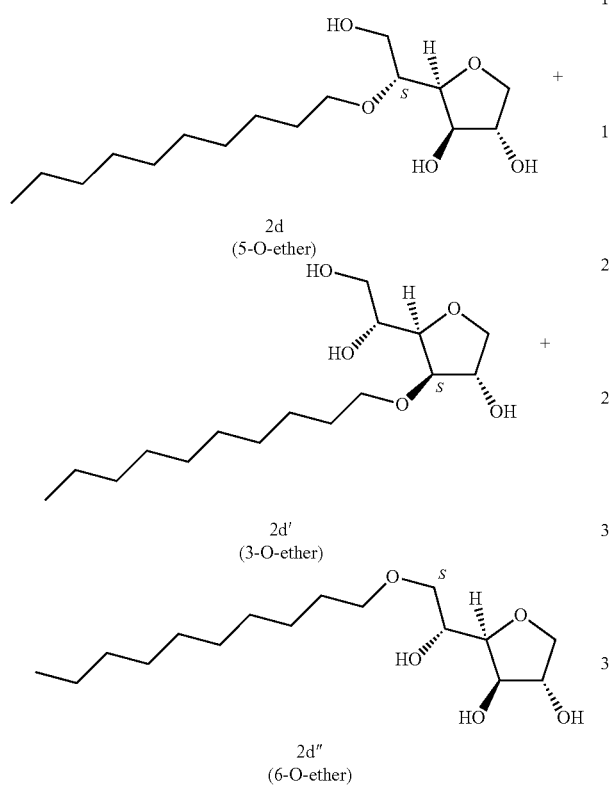

2d
(5-O-ether)

2d'
(3-O-ether)

2d"
(6-O-ether)

Decyl-1,4-d-sorbitan 2d, 2d' and 2d": The compounds were obtained from the 64:36 mixture of 5,6-O-decylidene-1,4-D-sorbitan 1d and 1d' and 3,5-O-decylidene-1,4-D-sorbitan 1d" and 1d'" (6.12 g, 20.2 mmol) according to the general procedure (B). After reaction, the residue is purified by chromatography on silica gel column (EtOAc/cyclohexane, 70:30→100:0 then EtOH/EtOAc 10:90) to give a mixture of sorbitan ether regioisomers 2d, 2d' and 2d" (3.66 g, 59%) in the form of a white solid. The product is a 32:16:52 mixture of 5-O-decyl-2d, 3-O-decyl-2d' and 6-O-decyl-1,4-D-sorbitan 2d" as determined by HPLC. NMR $^1$H (300 MHz, $d_6$-DMSO) $\delta_H$ for all the isomers: 0.85 (3H, t, J=6.9), 1.14-1.35 (14H, m), 1.37-1.55 (2H, m), 3.25-3.98 and 4.05-4.11 (10H, m, sorbitan protons+OCH$_2$ ethers), $\delta_H$ for isomer 2d: 4.31 (1H, t, J=5.4, OH$^6$), 4.82 (1H, d, J=4.3, OH$^3$), 4.99 (1H, d, J=2.9, OH$^2$), $\delta_H$ for isomer 2d': 4.31 (1H, t, J=5.4, OH$^6$), 4.35 (1H, d, J=5.5, OH$^5$), 5.06 (1H, d, J=3.3, OH$^2$), $\delta_H$ for isomer 2d": 4.53 (1H, d, J=5.8, OH$^5$), 4.80 (1H, d, J=4.3, OH$^3$), 4.98 (1H, d, J=1.9, OH$^2$); NMR $^{13}$C (75 MHz, $d_6$-DMSO) $\delta_C$ for isomer 2d (32%): 13.98 (CH$_3$), 22.16 (CH$_2$), 25.69 (CH$_2$), 28.79 (CH$_2$), 29.07 (CH$_2$), 29.10 (CH$_2$), 29.17 (CH$_2$), 29.92 (CH$_2$), 31.37 (CH$_2$), 62.01 (CH$_2$), 69.84 (CH$_2$), 73.16 (CH$_2$), 75.56 (CH), 76.48 (CH), 77.41 (CH), 79.30 (CH); $\delta_C$ for isomer 2d' (16%): 13.98 (CH$_3$), 22.16 (CH$_2$), 25.72 (CH$_2$), 28.79 (CH$_2$), 28.98 (CH$_2$), 29.07 (CH$_2$), 29.12 (CH$_2$), 29.57 (CH$_2$), 31.37 (CH$_2$), 64.18 (CH$_2$), 68.72 (CH), 69.55 (CH$_2$), 73.27 (CH), 73.60 (CH$_2$), 80.08 (CH), 83.96 (CH); $\delta_C$ for isomer 2d" (52%): 13.98 (CH$_3$), 22.16 (CH$_2$), 25.72 (CH$_2$), 28.79 (CH$_2$), 29.01 (CH$_2$), 29.07 (CH$_2$), 29.14 (CH$_2$), 29.35 (CH$_2$), 31.37 (CH$_2$), 67.53 (CH), 70.64 (CH$_2$), 73.37 (CH$_2$), 73.50 (CH$_2$), 75.69 (CH), 76.40 (CH), 80.35 (CH); HRMS (ESI+): [M+Na]+ $C_{16}H_{32}NaO_5$ calculated 327.2142, measured 327.2135 (+2.1 ppm); HPLC (C18 column, isocratic 50:50 $H_2O/CH_3CN$+0.1% $H_3PO_4$): $R_t$ 9.03 min (2d, 32%), 9.67 min (2d', 16%) and 11.61 min (2d", 52%).

Example 2e

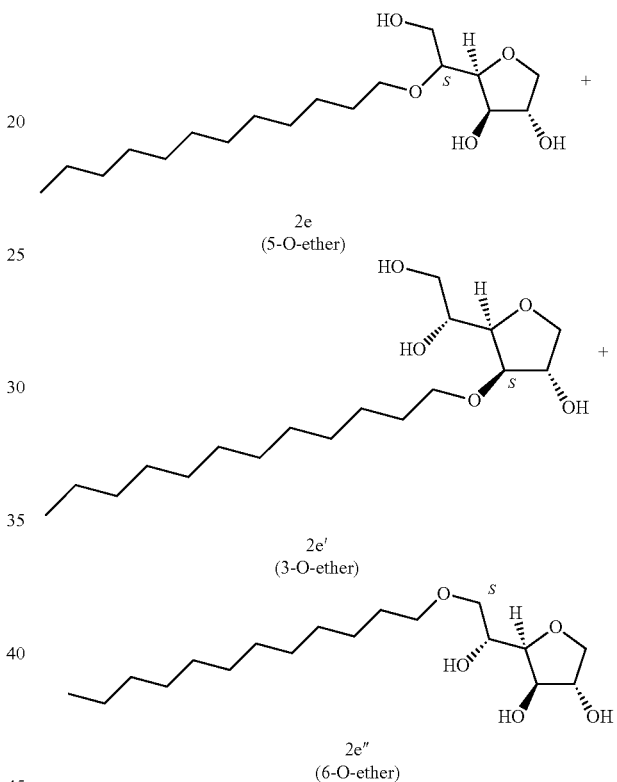

2e
(5-O-ether)

2e'
(3-O-ether)

2e"
(6-O-ether)

Dodecyl-1,4-d-sorbitan 2e, 2e' and 2e": The compounds were obtained from the 48:52 mixture of 5,6-O-dodecylidene-1,4-D-sorbitan 1e and 1e' and 3,5-O-dodecylidene-1,4-D-sorbitan 1e" and 1e'" (1.29 g, 3.92 mmol) according to the general procedure (B). After reaction, the residue is purified by chromatography on silica gel column (EtOAc/cyclohexane, 70:30→100:0 then EtOH/EtOAc 10:90) to give a mixture of sorbitan ether regioisomers 2e, 2e' and 2e" (0.72 g, 55%) in the form of a colorless oil. The product is a 27:33:40 mixture of 5-O-dodecyl-2e, 3-O-dodecyl-2e' and 6-O-dodecyl-1,4-D-sorbitan 2e" as determined by HPLC. NMR $^1$H (300 MHz, $d_6$-DMSO) $\delta_H$ for all the isomers: 0.85 (3H, t, J=6.9), 1.16-1.34 (18H, m), 1.38-1.54 (2H, m), 3.26-3.98 and 4.05-4.11 (10H, m, sorbitan protons+OCH$_2$ ethers), $\delta_H$ for isomer 2e: 4.32 (1H, t, J=5.5, OH$^6$), 4.84 (1H, d, J=3.7, OH$^3$), 5.00 (1H, d, J=2.8, OH$^2$), $\delta_H$ for isomer 2e': 4.32 (1H, t, J=5.5, OH$^6$), 4.37 (1H, d, J=5.4, OH$^5$), 5.06 (1H, d, J=3.3, OH$^2$), $\delta_H$ for isomer 2e": 4.55 (1H, d, J=5.8, OH$^5$), 4.82 (1H, d, J=4.1, OH$^3$), 4.99 (1H, d, J=2.1, OH$^2$); NMR $^{13}$C (75 MHz, $d_6$-DMSO) $\delta_C$ for isomer 2e (27%): 13.97 (CH$_3$), 22.11 (CH$_2$), 25.64 (CH$_2$), 28.74 (CH$_2$), 29.05 (3 CH$_2$), 29.08 (2 CH$_2$), 29.88 (CH$_2$), 31.32 (CH$_2$), 62.00 (CH$_2$), 69.81 (CH$_2$), 73.14 (CH$_2$), 75.52 (CH), 76.44 (CH), 77.38 (CH), 79.27 (CH); δ$_C$ for isomer 2e' (33%): 13.97 (CH$_3$), 22.11 (CH$_2$), 25.68 (CH$_2$), 28.74 (CH$_2$), 29.05 (3 CH$_2$), 29.08 (2 CH$_2$), 29.52 (CH$_2$), 31.32 (CH$_2$), 64.16 (CH$_2$), 68.69 (CH), 69.51 (CH$_2$), 73.22 (CH), 73.58 (CH$_2$), 80.06 (CH), 83.93 (CH); δ$_C$ for isomer 2e" (40%): 13.97 (CH$_3$), 22.11 (CH$_2$), 25.68 (CH$_2$), 28.74 (CH$_2$), 28.92 (CH$_2$), 28.96 (CH$_2$), 29.05 (2 CH$_2$), 29.08 (CH$_2$), 29.31 (CH$_2$), 31.32 (CH$_2$), 67.47 (CH), 70.59 (CH$_2$), 73.35 (CH$_2$), 73.48 (CH$_2$), 75.63 (CH), 76.35 (CH), 80.34 (CH); HRMS (ESI$^+$): [M+Na]$^+$ C$_{18}$H$_{36}$NaO$_5$ calculated 355.2455, found 355.2458 (−0.9 ppm); HPLC (C18 column, isocratic 50:50 H$_2$O/CH$_3$CN+0.1% H$_3$PO$_4$): R$_t$ 22.65 min (2e, 27%), 25.04 min (2e', 33%) and 30.81 min (2e", 40%).

Example 3

One-Pot Procedure for the Synthesis of a Sorbitan Ether

One Pot Synthesis of Sorbitan Ethers from 1,4-Sorbitan:

In a 100-mL round-bottomed flask, 1,4-sorbitan (10 g, 62 mmol) is dissolved in dry CPME (30 mL) in the presence of Na$_2$SO$_4$ (6.5 g, 50 mmol), under an argon atmosphere. Valeraldehyde (3.3 mL, 31 mmol) is added, dropwise, followed by Amberlyst 15 (530 mg, 20% m of valeraldehyde). The mixture is heated to 80° C. with magnetic stirring. After 3 hours, the hot mixture is filtered, washed with CPME (2×25 mL) and the filtrate is concentrated under low pressure. Without additional purification, the mixture is diluted in CPME (300 mL), dried on MgSO$_4$ and filtered. The filtrate is put in a 500-mL stainless-steel autoclave and 5%-Pd/C (3.3 mg) is added. The reactor is closed well and purged three times with hydrogen before the hydrogen is added under pressure (30 bar). The system is heated at 120° C. and stirred for 15 hours. After having been cooled to ambient temperature, the hydrogen under pressure is released, the reaction mixture is dissolved in absolute ethanol (250 mL) and filtered (0.01 micron Millipore Durapore filter). The filtrate is evaporated under low pressure and the residue (5.8 g) is purified by flash chromatography (EtOAc/cyclohexane 90:10 to 100:0, then EtOH/EtOAc 10:90). In this way a mixture of pentyl-(1,4)-sorbitan ethers (3.97 g, 56%) was obtained in the form of a colorless oil (purity >98% by NMR 1H).

Example 4

Measurement of Bacteriostatic Properties of Sorbitan Acetal and Ether Derivatives on Gram-Positive Bacteria The bacteriostatic properties of the derivatives are evaluated by measuring their minimum inhibitory concentration (MIC) on the bacteria tested. Such a measurement is made using the 96-well microplate microdilution method according to the conditions defined below.

Bacteria Tested:

The minimum inhibitory concentrations (MIC) are tested on Gram-positive bacterial strains according to the recommendations of the "*Clinical Laboratory Standards Institute*" (Clinical-Laboratory-Standards-Institute, 6th ed. Approved standard M100-S17. CLSI, Wayne, Pa., 2007).

The Gram-positive bacteria studied are as follows: *L. monocytogenes* (CIP 103575), *E. faecalis* (ATCC® 29212™) and *S. aureus* (ATCC® 292213™).

Inoculum Preparation:

The cultures studied, freshly isolated (after incubation on a blood agar at 37° C. for 18 h), are taken up in sterile water (10 mL) until a 0.5 McFarland (Mc) suspension i.e. 1 to 2×10$^8$ CFU (bacteria)/cm$^3$ is obtained. The bacterial suspension was then diluted to obtain a final concentration of 5×10$^5$ CFU/cm$^3$.

Preparation of Multiwell Plates for Reading the MIC:

Each well contains an identical quantity of Mueller-Hinton medium (a rich medium for bacterial culture) and bacteria with final 5×10$^5$ CFU/cm$^3$.

The test compounds of interest are solubilized in 2.5% m of ethanol before being diluted to different concentrations two by two.

On the multiwell plate, a first series has been planned comprising the culture medium without the test compound of interest. It corresponds to the growth control (control well). These controls serve as reference for comparing bacterial growth with that of the subsequent wells comprising different concentrations of the test compound of interest. The second series of wells comprises the mother solution for the test compound of interest for a concentration in the wells of 4 mM. Each series of wells was diluted two by two until the last series for a final concentration of 0.003 mM. Each concentration is duplicated in the same plate. The plate is incubated for 18 h at 37° C. The reading after incubation shows turbidity in the control wells (revealing bacterial growth). If there is antibacterial activity, the bacterial growth is inhibited, which means that no turbidity or bacterial residue is present. If the test compound inhibits this bacterial growth, it may correspond to either bacteriostatic activity in the molecule (inhibits bacterial growth), or to bactericidal activity in the molecule (causes bacteria to die).

Bacterial Count:

To determine whether the agents tested are bactericidal, the minimum bactericidal concentration (MBC) is determined. The MBC corresponds to the concentration leaving a number of bacterial survivors of <4 log. For this, a bacterial count is run from clear wells or without bacterial residue (C≤MIC). To do this, a dilution to 1/100 was conducted with the two wells with the same concentration before seeding on a blood agar using the Spiral technique. After 24 h of incubation at 37° C., the visual count allowed determination of the minimum concentration from which there is no bacterial growth.

Tests have been conducted on Gram-positive bacteria with sorbitan derivatives. The solutions of test compounds are diluted in ethanol at a solvent concentration that does not act on bacterial growth (2.5% m). After sterilization the solutions are diluted in water. The results obtained for antimicrobial tests on the 3 bacterial strains *L. monocytogenes* (CIP 103575), *E. faecalis* (ATCC® 29212™) and *S. aureus* (ATCC® 292213™) are summarized in Table 1.

TABLE 1

Antimicrobial results for sorbitan derivatives on Gram positives:
Minimum inhibitory concentration (MIC) in mmol/L

| Entry | Alkyl chain | Acetal (Ac) | | | Ether (Eth) | | |
|---|---|---|---|---|---|---|---|
| | | *L. monocytogenes* | *S. aureus* | *E. faecalis* | *L. monocytogenes* | *S. aureus* | *E. faecalis* |
| 1 | C5 | >4 | >4 | >4 | >4 | >4 | >4 |
| 2 | C6 | >4 | >4 | >4 | >4 | >4 | >4 |
| 3 | C8 | >4 | >4 | >4 | >4 | >4 | >4 |
| 4 | C10 | >4 | >4 | >4 | >4 | >4 | >4 |

Entry 1 (C5), Acetal: 36:64 isomeric mixture at the (5,6):(3,5) position
Entry 1 (C5), Ether: 33:26:41 isomeric mixture at the 3:5:6 position Entry 2 (C6), Acetal: 57:43 isomeric mixture at the (5,6):(3,5) position
Entry 2 (C6), Ether: 16:33:51 isomeric mixture at the 3:5:6 position Entry 3 (C8), Acetal: 61:39 isomeric mixture at the (5,6):(3,5) position
Entry 3 (C8), Ether: 22:33:45 isomeric mixture at the 3:5:6 position Entry 4 (C10), Acetal: 64:36 isomeric mixture at the (5,6):(3,5) position
Entry 4 (C10), Ether: 16:32:52 isomeric mixture at the 3:5:6 position TABLE 1-continued Antimicrobial results for sorbitan derivatives on Gram positives:
Minimum inhibitory concentration (MIC) in mmol/L

| Entry | Alkyl chain | Acetal (Ac) | | | Ether (Eth) | | |
|---|---|---|---|---|---|---|---|
| | | L. monocytogenes | S. aureus. | E. faecalis | L. monocytogenes | S. aureus. | E. faecalis |
| 5 | C12 | 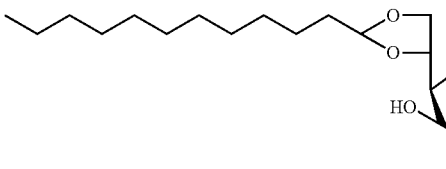 50:50 isomeric mixture at the (5,6):(3,5) position | | | 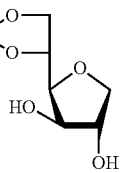 33:27:40 isomeric mixture at the 3:5:6 position | | |
| | | 0.03 | 0.12 | 0.03 | 0.12 | 0.12 | 0.12 |

According to observations on the 96-well microplates, the sorbitan ethers and acetals with aliphatic chains less than or equal to 10 carbons do not present antimicrobial properties because all the wells contain turbidity or a bacterial residue. The only bacterial inhibition is observed for compounds derived from dodecyl (entry 5).

Indeed, with concentrations below 12 mM, the sorbitan C12 acetal and ether inhibit the bacterial strains studied.

Example 5

Bactericidal Properties of Sorbitan Acetal and Ether Derivatives on Gram-positive Bacteria To determine the bactericidal effect of compounds presenting bacteriostatic properties, the wells no longer presenting turbidity were reseeded on agar. The results obtained after incubation for one night are presented in Table 2.

TABLE 2

Antimicrobial results for sorbitan derivatives on Gram positives: minimum inhibitory concentration (MIC) in mmol/L, minimum bactericidal concentration (MBC) in mmol/L (in italics)

| | | Sorbitan (Sorb) | |
|---|---|---|---|
| Entry | Bacteria | AcC12 | EthC12 |
| 1 | L. monocytogenes | 0.03 | 0.12 |
| 2 | S. aureus | 0.12 | 0.12 |
| 3 | E. faecalis | 0.03 | 0.12 |

Regarding the sorbitan derivatives, only the compounds containing 12 carbon chains and presenting bacterial inhibition have been analyzed. Sorbitan dodecylidene acetal has been revealed to be a bactericidal compound for L. monocytogenes and E. faecalis strains at 0.03 mM and bacteriostatic for S. aureus at 0.12 mM. To confirm that the properties measured on the acetals are indeed those of the amphiphilic compound and not its hydrolysis products, the properties of dodecanal were tested on the different bacterial strains and no antimicrobial activity was observed at concentrations less than or equal to 4 mM. Accordingly, the C12 sorbitan acetal is active as is and this activity does not come from the corresponding aldehyde. The mixture of sorbitan dodecyl ethers has an MBC of 0.12 mM for all the Gram-positive strains tested.

Therefore the conclusion can be drawn that sorbitan C12 acetals and ethers, even in the form of a mixture of regioisomers and diastereoisomers, present very interesting antimicrobial and bactericidal properties.

These results show that sorbitan derivatives may present a new range of biosourced bacteriostatic and bactericidal properties that is very active.

Example 6

Evaluation of Surfactant and Antimicrobial Properties

The physical, chemical and antimicrobial properties for the best products synthesized have been tested. These analyses show the different surfactant profiles, and the minimum inhibitory concentrations (MIC) for each compound on Gram-positive bacteria. The best surfactant and antimicrobial results are compared in Table 3.

TABLE 3

Comparison results between the critical micelle concentrations (CMC) and the minimum inhibitory concentrations (MIC) in (mmol/L) on the products of interest: Minimum inhibitory concentration (MIC) in mmol/L

| Entry | Compound | CMC (mM) | MIC (mM) | | |
|---|---|---|---|---|---|
| | | | *L. monocytogenes* | *S. aureus.* | *E. faecalis* |
| 1 | C12-Ac-Sorb | 0.034 | 0.03 | 0.12 | 0.03 |
| 1 | C12-Eth-Sorb | 0.091 | 0.12 | 0.12 | 0.12 |

For sorbitan dodecylidene (entry 1), the CMC value is in the MIC range. Sorbitan dodecyl ether has a slightly lower CMC (0.09 mM) than its MIC (0.12 mM) but these concentrations are relatively similar all the same (entry 2).

Example 7

Comparison Tests with Compounds Known in the Prior Art

The activity of sorbitan derivatives has been compared with that of compounds having similar structures or of a commercial compound like monolaurin (ML) in the table below.

TABLE 4

Comparison results between reference products (ML) and sorbitan acetals and ethers: Minimum inhibitory concentration (MIC) in mmol/L

| | Compounds tested | | |
|---|---|---|---|
| Bacteria | Compounds known in the prior art Monolaurin (ML) | C12-Eth-Sorb 33:27:40 isomeric mixture at the 3:5:6 position | C12-Ac-Sorb 50:50 isomeric mixture at the 3,5- and 5,6- position |
| *L. monocytogenes* | 0.04 | 0.12 | 0.03 |
| *S. aureus* | 0.04 | 0.12 | 0.12 |
| *E. faecalis* | ND | 0.12 | 0.03 |

The results obtained demonstrate that the derivatives are as effective as monolaurin (ML) since the difference in MIC obtained between the mixtures of acetals (C12AcSorb) or C12 sugar ethers (C12EthSorb) and monolaurin is low.

However, the stability of ether functions in biological medium was higher than the esters (sensitive to esterases), since the compounds comprising an ether function will therefore have prolonged activity over time which makes these derivatives of the compounds particularly advantageous.

Example 8

Measurement of Bacteriostatic Properties of a C12 Sorbitan Ether on Gram-positive Bacteria Since the best results were observed with compounds having a C12 alkyl group, experiments have been conducted on a wider panel of Gram-positive strains with a mixture of sorbitan ethers such as obtained according to the previous examples.

Inoculum Preparation:

The cultures studied, freshly isolated (after incubation on a blood agar at 37° C. for 18 h), are taken up in sterile water (10 mL) until a 0.5 McFarland (Mc) suspension i.e. at 1 to $2\times10^8$ CFU (bacteria)/cm$^3$ is obtained. The bacterial suspension was then diluted to obtain a final concentration of $1\times10^6$ CFU/cm$^3$.

Preparation of Multiwell Plates for Reading the MIC:

Each well contains an identical quantity of Mueller-Hinton medium (a rich medium for bacterial culture) and bacteria with final $0.5\times10^6$ CFU/cm$^3$.

The test compounds of interest are solubilized in ethanol or DMSO at 25 mg/mL before being diluted to different concentrations two by two. On the multiwell plate, a first series has been planned comprising the culture medium without the test compound of interest. It corresponds to the growth control (control well). These controls serve as reference for comparing bacterial growth with that of the subsequent wells comprising different concentrations of the test compound of interest. The second series of wells comprises the mother solution for the test compound of interest for a concentration in the wells of 256 mg (7 mM). Each series of wells was diluted two by two until the last series for a final concentration of 0.25 mg/L (0.0007 mM). Each concentration is duplicated in the same plate. The plate is incubated for 18 h at 37° C. The reading after incubation shows turbidity in the control wells (revealing bacterial growth). If there is antibacterial activity, the bacterial growth is inhibited, which means that no turbidity or bacterial residue is present.

The minimum inhibitory concentrations (MIC) are tested on Gram-positive bacterial strains according to the recommendations of the "*Clinical Laboratory Standards Institute*" (Clinical-Laboratory-Standards-Institute, 6th ed. Approved standard M100-S17. CLSI, Wayne, Pa., 2007). The clinical strains have been isolated in the Hospice de Lyon.

The Gram-positive Bacteria Studied are as Follows:

*Staphylococci S. aureus*: ATCC® 29213™, ATCC 25923,

*Staphylococci* strains Methicillin-resistant *S. aureus* (LacDeleo USA 300), (MU 3), (HT 2004-0012), LY 199-0053, (HT 2002-0417), (HT 2006-1004),

*Staphylococci* strains Daptomycin-resistant *S. aureus* (ST 2015-0188), (ST 2014 1288).

*Enterococci: E. faecalis* (ATCC® 29212™), clinical enterococci strains *E. faecalis* isolated from urines: strain 015206179901 (hereinafter 9901), strain 015205261801 (hereinafter 1801)

*Enterococci: E. faecium* (CIP 103510), clinical strains of *Enterococci E. faecium*: Van A 0151850763 (hereinafter Van A); strain 015 205731401 (hereinafter 1401),

*Listeria: L. monocytogenes* (CIP 103575), clinical strain isolated from hemoculture (015189074801, LM1), a strain isolated from cerebrospinal liquid (015170199001, LM2), clinical strains isolated from hemoculture (015181840701, LM3).

Inoculum Preparation:

The cultures studied, freshly isolated (after incubation on a blood agar at 37° C. for 18 h), are taken up in sterile water (10 mL) until a 0.5 McFarland (Mc) suspension i.e. at $10^8$ CFU (bacteria)/cm$^3$ is obtained. The bacterial suspension was then diluted to obtain a final concentration of $10^6$ CFU/cm$^3$.

Results for the Strains of Genus *Staphylococcus*

TABLE 5

Antimicrobial results for a sorbitan ether on different strains of *Staphylococcus Aureus*: Minimum inhibitory concentration (MIC) in mg/L

| | | *Staphylococcus* | | | | | | | |
|---|---|---|---|---|---|---|---|---|---|
| ATCC 25923 | ATCC 29213 | USA 300 | MU 3 | HT 2004-0012 | LY 199-0053 | HT 2002-0417 | HT 2006-1004 | ST 2015-0188 | ST 2014 1288 |
| 32 | 32 | 32 | 64 | 32 | 32 | 32 | 32 | 64 | 64 |

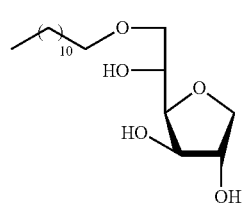

C12-Eth-Sorb

According to observations on the 96-well microplates, the sorbitan C12 ether (C12-Eth-Sorb) is active against the *Staphylococcus* strains tested (32<MIC<64 mg/L).

Results for the Strains of Genus *Enterococcus*

TABLE 6

Antimicrobial results for a sorbitan ether on different strains of enterococcus. Minimum inhibitory concentration (MIC) in mg/L

| | Enterococcus | | | | | |
|---|---|---|---|---|---|---|
| | ATCC 29212 | Van A | CIP 103510 | 1401 | 9901 | 1801 |
| C12-Eth-Sorb | 8 | 16 | 16 | 8 | 16 | 8 |

Good antibacterial activity for the sorbitan C12 ether for all the *Enterococcus* strains tested 8<MIC<16 mg/L.

Results for Strains of the *Listeria* Genus

TABLE 7

Antimicrobial results for a sorbitan ether on different strains of *Listeria*. Minimum inhibitory concentration (MIC) in mg/L.

| | Listeria | | | |
|---|---|---|---|---|
| | CIP 103575 | LM1 | LM2 | LM3 |
| C12-Eth-Sorb | 32 | 16 | 32 | 32 |

Good antibacterial activity for the sorbitan C12 ether for all the *Listeria* strains tested 16<MIC<32 mg/L.

The invention claimed is:

1. A method for disinfection or prevention of bacterial colonization by Gram-positive bacteria of a substrate comprising putting the substrate into contact with a bactericidal or bacteriostatic composition comprising a mixture of regioisomers of an alkyl acetal or an alkyl ether of sorbitan, arlitan, mannitan or a pharmaceutically acceptable salt thereof, wherein the alkyl group comprises between 11 to 18 carbon atoms, wherein said alkyl acetal group is in the 2,3-O—; 3,5-O- and/or 5,6-O- positions or said alkyl ether group is in the 2-O, 3-O-, 5-O- and/or 6-O- positions.

2. The method as claimed in claim 1 characterized in that the alkyl group comprises 11 to 13 carbon atoms.

3. The method as claimed in claim 1 characterized in that the Gram-positive bacteria are bacteria from the phylum of Firmicutes, typically of the class of Bacilli in particular chosen from bacteria of the order of Lactobacillales or Bacillales.

4. The method as claimed in claim 3 characterized in that the Gram-positive bacteria are bacteria from the order of Bacillales chosen from the family of Alicyclobacillaceae, Bacillaceae, Caryophanaceae, Listeriaceae, Paenibacillaceae, Pasteuriaceae, Planococcaceae, Sporolactobacillaceae, Staphylococcaceae, Thermoactinomycetacea and Turicibacteriaceae.

5. The method as claimed in claim 3 characterized in that the Gram-positive bacteria are bacteria from the family of Listeriaceae such as a bacterium of the genus *Brochothrix* or *Listeria* typically chosen from *L. fleischmannii, L. grayi, L. innocua, L. ivanovii, L. marihii, L. monocytogenes, L. rocourtiae, L. seeligeri, L. weihenslephanensis* and *L. welshimeri*.

6. The method as claimed in claim 3 characterized in that the Gram-positive bacteria are bacteria from the family of Staphylococcaceae chosen from bacteria from the genus *Staphylococcus, Gemella, Jeolgalicoccus, Macrococcus, Salinicoccus* and *Nosocomiicoccus*.

7. The method as claimed in claim 6 characterized in that the Gram-positive bacteria are bacteria from the genus *Staphylococcus* chosen from *S. arlettae, S. agnelis, S. aureus, S. auricularis, S. capitis, S. caprae, S. carnosus, S. caseolyticus, S. chromogenes, S. cohnii, S. condimenti, S. delphini, S. devriesei, S. epidermidis, S. equorum, S. felis, S. fleurettii, S. gallinarum, S. haemolyticus, S. hominis, S. hyicus, S. intermedius, S. kloosii, S. leei, S. lentus, S. lugdunensis, S. lutrae, S. massiliensis, S. microti, S. muscae, S. nepalensis, S. pasteuri, S. pettenkoferi, S. piscifermentans, S. pseudintermedius, S. pseudolugdunensis, S. pulvereri, S. rostri, S. saccharolyticus, S. saprophyticus, S. schleiferi, S. sciuri, S. simiae, S. simulans, S. stepanovicii, S. succinus, S. vitulinus, S. warneri* and *S. xylosus*.

8. The method as claimed in claim 3 characterized in that the Gram-positive bacteria are Lactobacillales chosen from a family of Aerococcaceae, Carnobacteriaceae, Enterococcaceae, Lactobacillaceae, Leuconostocaceae and Streptococcaceae.

9. The method as claimed in claim 8 characterized in that the Gram-positive bacteria are bacteria from the family of Enterococcaceae chosen from bacteria from the genus *Bavariicoccus, Catellicoccus, Enterococcus, Melissococcus, Pilibacler, Tetragenococcus, Vagococcus*.

10. The method as claimed in claim 9 characterized in that the Gram-positive bacteria are bacteria from the genus *Enterococcus* chosen from *E. malodoratus, E. avium, E. durans, E. faecalis, E. faecium, E. gallinarum, E. hirae,* and *E. solitarius*.

11. The method as claimed in claim 1 characterized in that the bactericidal or bacteriostatic composition is incorporated in a food, cosmetic, pharmaceutical, phytosanitary, veterinary or surface treatment composition.

12. The method as claimed in claim 1 wherein the method is used externaly for a dermatological product for external purpose.

13. The method as claimed in claim 1 wherein the method is for cleaning, sterilizing or purifying said substrate.

14. The method as claimed in claim 1 wherein the method is for the treatment or prevention of bacterial infections by Gram-positive bacteria and wherein the bactericidal or bacteriostatic composition is administered topically to a subject in need thereof.

15. The method as claimed in claim 14 in which the infection by Gram-positive bacteria is an infection of the skin or mucous membranes, wherein the infection is chosen from folliculitis, an abcess, paronychia, a boil, impetigo, an infection between the digits, anthrax (staphylococcal anthrax), cellulitis, a secondary wound infection, otitis, sinusitis, hidradenitis, infectious mastitis, a post-traumatic skin infection or an infection on burnt skin.

16. The method as claimed in claim 9 characterized in that the Gram-positive bacteria are bacteria from the genus *Enterococcus* chosen from *E. avium, E. durans, E. faecalis* and *E. faecium*.

* * * * *